(12) United States Patent
Moore et al.

(10) Patent No.: US 11,957,439 B2
(45) Date of Patent: *Apr. 16, 2024

(54) CLOSED CAVITY ADJUSTABLE SENSOR MOUNT SYSTEMS AND METHODS

(71) Applicant: Stryker Corporation, Kalamazoo, MI (US)

(72) Inventors: Frederick Allen Moore, Vancouver (CA); Lesley Myron Otsig, New Westminster (CA); Muhammad Nasir Al-Din bin Zulkafly, Vancouver (CA); Theodore Drew Fast Husby, Vancouver (CA)

(73) Assignee: Stryker Corporation, Kalamazoo, MI (US)

(*) Notice: Subject to any disclaimer, the term of this patent is extended or adjusted under 35 U.S.C. 154(b) by 274 days.

This patent is subject to a terminal disclaimer.

(21) Appl. No.: 17/498,636

(22) Filed: Oct. 11, 2021

(65) Prior Publication Data
US 2022/0047172 A1   Feb. 17, 2022

Related U.S. Application Data

(63) Continuation of application No. 15/625,710, filed on Jun. 16, 2017, now Pat. No. 11,141,071.
(Continued)

(51) Int. Cl.
*A61B 5/0205* (2006.01)
*A61B 1/00* (2006.01)
(Continued)

(52) U.S. Cl.
CPC ............ *A61B 5/0205* (2013.01); *A61B 1/043* (2013.01); *A61B 5/02007* (2013.01);
(Continued)

(58) Field of Classification Search
CPC ... A61B 5/0205; A61B 1/043; A61B 5/02007; A61B 5/14546; A61B 1/00; A61B 5/00;
(Continued)

(56) References Cited

U.S. PATENT DOCUMENTS 4,621,782 A  11/1986 Carlson
4,641,635 A  2/1987 Yabe
(Continued)

OTHER PUBLICATIONS

European Extended Search Report dated Jan. 14, 2020, directed to EP Application No. 17812366.7; 8 pages.
(Continued)

*Primary Examiner* — Patrick Fernandes
*Assistant Examiner* — Nicholas A Robinson
(74) *Attorney, Agent, or Firm* — Morrison & Foerster LLP

(57) ABSTRACT

Closed cavity adjustable sensor mount systems include a sealed, closed cavity enclosing a sensor and forming a closed cavity sensor assembly. The closed cavity sensor assembly may be tilted and/or translated relative to a platform in order to adjust the orientation of the sensor to align it with an imaging optical axis. Following alignment, the closed cavity sensor assembly may be permanently or reversibly fixed in place. The closed cavity adjustable sensor mount systems may be part of medical imaging systems such as endoscopic imaging systems and/or open field imaging systems.

13 Claims, 23 Drawing Sheets

Related U.S. Application Data

(60) Provisional application No. 62/351,236, filed on Jun. 16, 2016.

(51) Int. Cl.
  *A61B 1/04* (2006.01)
  *A61B 5/00* (2006.01)
  *A61B 5/02* (2006.01)
  *A61B 5/145* (2006.01)
  *A61K 49/00* (2006.01)

(52) U.S. Cl.
  CPC ...... *A61B 5/14546* (2013.01); *A61K 49/0017* (2013.01); *A61K 49/0045* (2013.01); *A61B 1/00* (2013.01); *A61B 5/00* (2013.01); *A61B 5/418* (2013.01)

(58) Field of Classification Search
  CPC . A61B 5/418; A61K 49/0017; A61K 49/0045
  See application file for complete search history.

(56) References Cited

U.S. PATENT DOCUMENTS

| | | | |
|---|---|---|---|
| 4,846,509 A | 7/1989 | Moore | |
| 4,973,145 A | 11/1990 | Kirkwood | |
| 6,277,064 B1 * | 8/2001 | Yoon | A61B 1/051 600/173 |
| 9,173,554 B2 | 11/2015 | Fengler | |
| 2003/0169333 A1 | 9/2003 | Yazawa et al. | |
| 2005/0275311 A1 * | 12/2005 | Choi | B29C 43/021 310/323.05 |
| 2006/0245050 A1 | 11/2006 | Uchida | |
| 2008/0151041 A1 | 6/2008 | Shafer | |
| 2010/0171018 A1 | 7/2010 | Grant | |
| 2010/0245549 A1 | 9/2010 | Allen | |
| 2011/0115975 A1 | 5/2011 | Konishi | |
| 2013/0096376 A1 | 4/2013 | Takei | |
| 2013/0323521 A1 | 12/2013 | Xia | |

OTHER PUBLICATIONS

International Preliminary Report on Patentability dated Dec. 27, 2018, directed to International Application No. PCT/CA2017/050742; 8 pages.

International Search Report dated Sep. 18, 2017, directed to International Application No. PCT/CA2017/050742; 6 pages.

Invitation to Pay Additional Fees, and, where Applicable, Protest Fee dated Jul. 18, 2017, directed to International Application No. PCT/CA2017/050742; 3 pages.

Moore et al., U.S. Notice of Allowance and Fee(s) Due dated Jun. 10, 2021, directed to U.S. Appl. No. 15/625,710; 16 pages.

Moore et al., U.S. Office Action dated Aug. 31, 2020, directed to U.S. Appl. No. 15/625,710; 20 pages.

Moore et al., U.S. Office Action dated Feb. 20, 2020, directed to U.S. Appl. No. 15/625,710; 17 pages.

Moore et al., U.S. Office Action dated Feb. 26, 2021, directed to U.S. Appl. No. 15/625,710; 16 pages.

Moore et al., U.S. Office Action dated Jul. 29, 2019, directed to U.S. Appl. No. 15/625,710; 25 pages.

Office Action dated Nov. 7, 2019, directed to CA Application No. 3,027,636; 4 pages.

Office Action dated Sep. 9, 2020, directed to CA Application No. 3,027,636; 4 pages.

Written Opinion dated Sep. 18, 2017, directed to International Application No. PCT/CA2017/050742; 6 pages.

Office Action dated Jun. 2, 2022, directed to EP Application No. 17 812 366.7; 4 pages.

* cited by examiner

CLOSED CAVITY ADJUSTABLE SENSOR MOUNT SYSTEMS AND METHODS

CROSS-REFERENCE TO RELATED APPLICATIONS

This application is a continuation of U.S. patent application Ser. No. 15/625,710, filed Jun. 16, 2017, which claims priority to U.S. Provisional Application No. 62/351,236, filed Jun. 16, 2016, each of which are hereby incorporated by reference in their entirety.

FIELD OF THE INVENTION

The present disclosure relates generally to medical illumination and imaging. More specifically, the disclosure relates to adjustable sensor mount systems and methods.

BACKGROUND OF THE INVENTION

Optical performance of imaging systems may suffer from sensor misalignment and contamination. Image quality may be especially sensitive to misalignment when using a high resolution sensor, or if the imaging optics of the system feature a large aperture. Tilt-adjustable imaging sensors may fail to maintain sensor alignment for extended periods and/or over repeated use, and may be too large and bulky for compact imaging systems. Similarly, image quality may be adversely affected by dust and debris. Sensor mounts with adjustable moving parts may further decrease optical performance by releasing debris particles due to wear in the vicinity of the sensor.

In order to achieve a desired image quality, it may be desirable to have compact, tilt-adjustable imaging sensors that allow for fine adjustment of sensor tilt alignment while also allowing for reinforced fixation after sensor tilt alignment. It may also be desirable to have sensors located within sealed, closed compartments to protect against or limit dust and debris.

SUMMARY OF THE INVENTION

Described herein are adjustable sensor mount systems and methods. The adjustable sensor mounts may include a platform and a sensor assembly. The sensor assembly may form a sealed, closed cavity around a sensor. In some variations, the platform may comprise a concave surface, while the sensor assembly may comprise a convex surface having a corresponding and complementary shape to the concave surface of the platform. The adjustable sensor mount may be configured such that the sensor can be tilted about at least one axis via movement of the sensor assembly relative to the platform. In some variations, the sensor may be able to be tilted about two axes. In some variations, the alignment of the sensor may be adjusted using one or more fasteners (e.g., screws). The one or more fasteners may be configured to tilt the sensor assembly, and thus the sensor, while being tightened and/or loosened.

The adjustable sensor mounts may be configured for fixation after a desired sensor alignment has been achieved. In some variations, the orientation of the sensor may be fixed by bonding the sensor assembly to the platform. At least a portion of the sensor assembly may optionally comprise a Ultraviolet (UV)-transmitting material, such as but not limited to glass, in order to allow for Ultraviolet (UV)-activation of a bonding glue. When a bonding glue is used for fixation, the glue may in some variations comprise fixed-diameter beads to maintain an invariant bond gap between the joint surfaces.

In some variations, described here are adjustable sensor mount systems comprising a platform and a closed cavity sensor assembly, where the closed cavity sensor assembly comprises a sensor, and the closed cavity sensor assembly is attached to the platform. The adjustable sensor mount systems may comprise a first configuration in which the sensor is rotatable about at least one axis via movement of the closed cavity sensor assembly relative to the platform, and a second configuration in which the closed cavity sensor assembly is fixed relative to the platform. In the second configuration, the closed cavity sensor assembly may be fixed to the platform using fasteners (e.g., screws) and/or bonding glue. The closed cavity sensor assembly may be permanently or reversibly fixed to the platform in the second configuration.

In some variations, described here are adjustable sensor mount systems comprising a flexure assembly and an adjustable sensor mount. The adjustable sensor mount may comprise a closed cavity sensor assembly, and the closed cavity sensor assembly may comprise a sensor. The closed cavity sensor assembly may be attachable to the flexure assembly, such that the sensor is configured to be tilted about at least one axis via movement of the closed cavity sensor assembly. In some variations, the sensor may be configured to be tilted about two axes. The flexure assembly may comprise a top sensor mount plane that is configured to tilt. The top sensor mount plane may tilt due to pressure applied to a side of the flexure assembly, such as applied by a screw. The adjustable sensor mount may be attachable to the top sensor mount plane. The adjustable sensor mount may comprise a flexure plate configured to allow tilting of the sensor. For example, the flexure plate may comprise a plurality of channels through the flexure plate. In some variations, the adjustable sensor mount may additionally or alternatively comprise an X-Y platform configured to allow translation of the sensor.

Also described herein are endoscopic and open field medical imaging systems comprising an adjustable sensor mount. The medical imaging systems may generally comprise a laparoscope or an open field imaging head, a light source assembly configured to provide illumination to the laparoscope, and an image acquisition assembly comprising an adjustable sensor mount. The adjustable sensor mount may comprise a closed cavity sensor assembly. In some variations, the light source assembly may comprise a visible light source and/or an excitation light source. The adjustable sensor mount may further comprise a platform having a surface with a corresponding and complementary shape to a surface of the closed cavity sensor assembly. The closed cavity sensor assembly may be rotatable relative to the platform.

Also described herein are methods for aligning a sensor of an imaging system. When the sensor comprises a closed cavity sensor assembly movably attached to a platform and a plurality of fasteners (e.g., screws), the method may comprise tightening or loosening at least one of the plurality of fasteners to tilt the sensor assembly relative to the platform. The method may further comprise fixing the sensor assembly to the platform after alignment. In some variations the sensor assembly may be fixed using a plate, which may for example be attached to both the platform and the closed cavity sensor assembly. In these or other variations, the sensor assembly may be attached to the platform using a bonding glue. The bonding glue may have fixed-diameter beads and/or be Ultraviolet (UV)-activated.

In other methods described here, the methods may be used for aligning a sensor of an imaging device camera assembly. The imaging device camera assembly may comprise an adjustable sensor mount comprising a closed cavity sensor assembly. The camera assembly may be attached to an alignment adjustment jig, and the alignment adjustment jig may be used to adjust the alignment of the closed cavity sensor assembly. To adjust the closed cavity sensor assembly, it may be tilted about one or more axes and/or translated. In some variations, the alignment adjustment jig may comprise a first set of stages configured to tilt the closed cavity sensor assembly, and a second set of stages configured to translate the closed cavity sensor assembly. The closed cavity sensor assembly may be fixed in place after being adjusted.

In some embodiments, an adjustable sensor mount for use with an imaging system comprises: a closed cavity sensor assembly comprising a sensor, wherein the sensor is configured to be tilted about at least one axis via movement of the closed cavity sensor assembly.

In some embodiments, the adjustable sensor mount further comprises a platform having a first shape, wherein the closed cavity sensor has a second shape that is corresponding and complementary to the first shape of the platform.

In some embodiments of the adjustable sensor mount, the first shape comprises a concave surface.

In some embodiments of the adjustable sensor mount, the second shape comprises a convex surface.

In some embodiments of the adjustable sensor mount, the sensor is configured to be tilted about at least one axis via movement of the closed cavity sensor assembly relative to the platform.

In some embodiments of the adjustable sensor mount, the sensor is configured to be tilted about two axes via movement of the closed cavity sensor assembly relative to the platform.

In some embodiments, the adjustable sensor mount further comprises a fastener, wherein the fastener is configured to tilt the closed cavity sensor assembly when tightened.

In some embodiments of the adjustable sensor mount, the fastener is a screw.

In some embodiments, the adjustable sensor mount further comprises a fastener, wherein the fastener is configured to tilt the closed cavity sensor assembly when loosened.

In some embodiments of the adjustable sensor mount, the fastener is a screw.

In some embodiments of the adjustable sensor mount, at least a portion of the closed cavity sensor assembly comprises a UV-transmitting material In some embodiments of the adjustable sensor mount, at least a portion of the closed cavity sensor assembly comprises glass.

In some embodiments, a first adjustable sensor mount system comprises: a closed cavity sensor assembly comprising a sensor, wherein the adjustable sensor mount system comprises a first configuration in which the sensor is rotatable about at least one axis, and wherein the adjustable sensor mount system comprises a second configuration in which the closed cavity sensor assembly is fixed.

In some embodiments, the first adjustable sensor mount system further comprises a platform, wherein the sensor is rotatable in the first configuration about at least one axis via movement of the closed cavity sensor assembly relative to the platform, and wherein the closed cavity sensor assembly is fixed in the second configuration relative to the platform.

In some embodiments of the first adjustable sensor mount system, in the second configuration, the closed cavity sensor assembly is fixed relative to the platform using screws.

In some embodiments of the first adjustable sensor mount system, in the second configuration, the closed cavity sensor assembly is bonded to the platform.

In some embodiments of the first adjustable sensor mount system, in the second configuration, fixed-diameter beads are located between the closed cavity sensor and the platform.

In some embodiments, a first adjustable sensor mount system comprises: a flexure assembly; and an adjustable sensor mount comprising a closed cavity sensor assembly, wherein the closed cavity sensor assembly comprises a sensor, and wherein the closed cavity sensor assembly is attachable to the flexure assembly, wherein the sensor is configured to be tilted about at least one axis.

In some embodiments of the second adjustable sensor mount system, the sensor is configured to be tilted about at least one axis via movement of the closed cavity sensor assembly.

In some embodiments of the second adjustable sensor mount system, the sensor is configured to be tilted about two axes.

In some embodiments of the second adjustable sensor mount system, the flexure assembly comprises a top sensor mount plane configured to tilt when pressure is applied to a side of the flexure assembly.

In some embodiments of the second adjustable sensor mount system, the closed cavity sensor assembly is attachable to the top sensor mount plane.

In some embodiments of the second adjustable sensor mount system, the adjustable sensor mount comprises a flexure plate configured to allow tilting of the sensor.

In some embodiments of the second adjustable sensor mount system, the flexure plate comprises a plurality of channels through the flexure plate.

In some embodiments of the second adjustable sensor mount system, the adjustable sensor mount comprises an X-Y platform configured to allow translation of the sensor.

In some embodiments, a medical imaging system comprises: an imaging head; a light source assembly configured to provide illumination to the laparoscope; and an image acquisition assembly comprising an adjustable sensor mount.

In some embodiments of the medical imaging system, the adjustable sensor mount comprises a closed cavity sensor assembly.

In some embodiments of the medical imaging system, the adjustable sensor mount comprises a multi-chip sensor assembly comprising a prism and at least two image sensors.

In some embodiments of the medical imaging system, the light source assembly comprises a visible light source and an excitation light source.

In some embodiments of the medical imaging system, the adjustable sensor mount further comprises a platform having a surface with a corresponding and complementary shape to a surface of the sensor assembly, and wherein the sensor assembly is rotatable about at least one axis relative to the platform.

In some embodiments of the medical imaging system, the system is an endoscopic medical imaging system and the imaging head is a laparoscope.

In some embodiments of the medical imaging system, the system is an open field medical imaging system and the imaging head is an open field imaging head.

In some embodiments, a first method is provided for aligning a sensor of an imaging system comprising a platform, a closed cavity sensor assembly movably attached to the platform, and a plurality of fasteners, the first method comprising: tightening or loosening at least one of the plurality of fasteners to tilt the sensor assembly relative to the platform; and fixing the sensor assembly to the platform.

In some embodiments of the first method, the sensor assembly is attached to the platform by a plate.

In some embodiments of the first method, the sensor assembly is attached to the platform by bonding glue.

In some embodiments of the first method, the bonding glue comprises fixed-diameter beads.

In some embodiments of the first method, the bonding glue is UV-activated.

In some embodiments, a second method for aligning a sensor of an imaging device camera assembly is provided, wherein the camera assembly comprises an adjustable sensor mount, wherein the adjustable sensor mount comprises a closed cavity sensor assembly, the second method comprising: attaching the camera assembly to an alignment adjustment jig; and adjusting the alignment of the closed cavity sensor assembly, wherein adjusting the alignment of the closed cavity sensor assembly comprises at least one of tilting the closed cavity sensor assembly about an axis and translating the closed cavity sensor assembly.

In some embodiments of the second method, the alignment adjustment jig comprises a first set of stages configured to tilt the closed cavity sensor assembly, and a second set of stages configured to translate the closed cavity sensor assembly.

In some embodiments, the second method further comprises fixing the closed cavity sensor assembly after adjusting the alignment.

In some embodiments, an alignment jig configured for aligning an adjustable sensor mount is provided, wherein the adjustable sensor mount comprises a closed cavity sensor assembly, the alignment jig comprising: an adjustment stage assembly configured to allow tilting and translation of the closed cavity sensor assembly.

In some embodiments of the alignment jig, the adjustment stage assembly is configured to be mounted on a set of rail.

In some embodiments of the alignment jig, the adjustment stage assembly comprises: a first set of stages configured to adjust tilt of the closed cavity sensor assembly; a second set of stages configured to adjust alignment of the closed cavity sensor assembly.

In some embodiments of the alignment jig, the first set of stages is configured such that stages in the first set are stacked with different radii, such that the stages have the same pivot point.

In some embodiments of the alignment jig, the adjustment stage assembly is configured to be held in place by compression springs.

In some embodiments of the alignment jig, the adjustment stage assembly is configured to contact the closed cavity sensor assembly via one or more kinematic balls.

In some embodiments of the alignment jig, the kinematic balls are located in indentations in a closed cavity platform of the closed cavity sensor assembly.

In some embodiments of the alignment jig, the adjustable sensor mount is configured to be fixed using a bridge assembly after alignment via the adjustment stage assembly.

In some embodiments, a kit for fluorescence imaging comprises an adjustable sensor mount having any one or more characteristics as described above, an adjustable sensor mount system having any one or more characteristics as described above, an adjustable sensor mount system having any one or more characteristics as described above, a medical imaging system having any one or more characteristics as described above, or an alignment jig having any one or more characteristics as described above.

In some embodiments, the kit further comprises a fluorescence imaging agent.

In some embodiments, a fluorescence imaging agent for medical imaging is provided for use with an adjustable sensor mount having any one or more characteristics as described above, an adjustable sensor mount system having any one or more characteristics as described above, an adjustable sensor mount system having any one or more characteristics as described above, a medical imaging system having any one or more characteristics as described above, or an alignment jig having any one or more characteristics as described above.

In some embodiments of the fluorescence imaging agent, the medical imaging comprises blood flow imaging, tissue perfusion imaging, and/or lymphatic imaging comprises blood flow imaging, tissue perfusion imaging, and/or lymphatic imaging during an invasive surgical procedure, a minimally invasive surgical procedure, or during a non-invasive surgical procedure.

In some embodiments of the fluorescence imaging agent, the invasive surgical procedure comprises a cardiac-related surgical procedure or a reconstructive surgical procedure.

In some embodiments of the fluorescence imaging agent, the cardiac-related surgical procedure comprises a cardiac coronary artery bypass graft (CABG) procedure.

In some embodiments of the fluorescence imaging agent, the CABG procedure is on pump or off pump.

In some embodiments of the fluorescence imaging agent, the non-invasive surgical procedure comprises a wound care procedure.

In some embodiments of the fluorescence imaging agent, the lymphatic imaging comprises identification of a lymph node, lymph node drainage, lymphatic mapping, or a combination thereof.

In some embodiments of the fluorescence imaging agent, the lymphatic imaging relates to the female reproductive system.

In some embodiments, use of an adjustable sensor mount having any one or more characteristics as described above, an adjustable sensor mount system having any one or more characteristics as described above, an adjustable sensor mount system having any one or more characteristics as described above, a medical imaging system having any one or more characteristics as described above, or an alignment jig having any one or more characteristics as described above for lymphatic imaging is provided.

In some embodiments, use of an adjustable sensor mount having any one or more characteristics as described above, an adjustable sensor mount system having any one or more characteristics as described above, an adjustable sensor mount system having any one or more characteristics as described above, a medical imaging system having any one or more characteristics as described above, or an alignment jig having any one or more characteristics as described above for lymphatic imaging, blood flow imaging, tissue perfusion imaging, or a combination thereof is provided.

BRIEF DESCRIPTION OF THE DRAWINGS

Features will become apparent to those of ordinary skill in the art by describing in detail exemplary embodiments with reference to the attached drawings in which.

DETAILED DESCRIPTION OF THE INVENTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. Various devices, systems, methods, processors, kits and imaging agents are described herein. Although at least two variations of the devices, systems, methods, processors, kits and imaging agents are described, other variations may include aspects of the devices, systems, methods, processors, kits and imaging agents described herein combined in any suitable manner having combinations of all or some of the aspects described.

Generally, corresponding or similar reference numbers will be used, when possible, throughout the drawings to refer to the same or corresponding parts.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Figure 1:
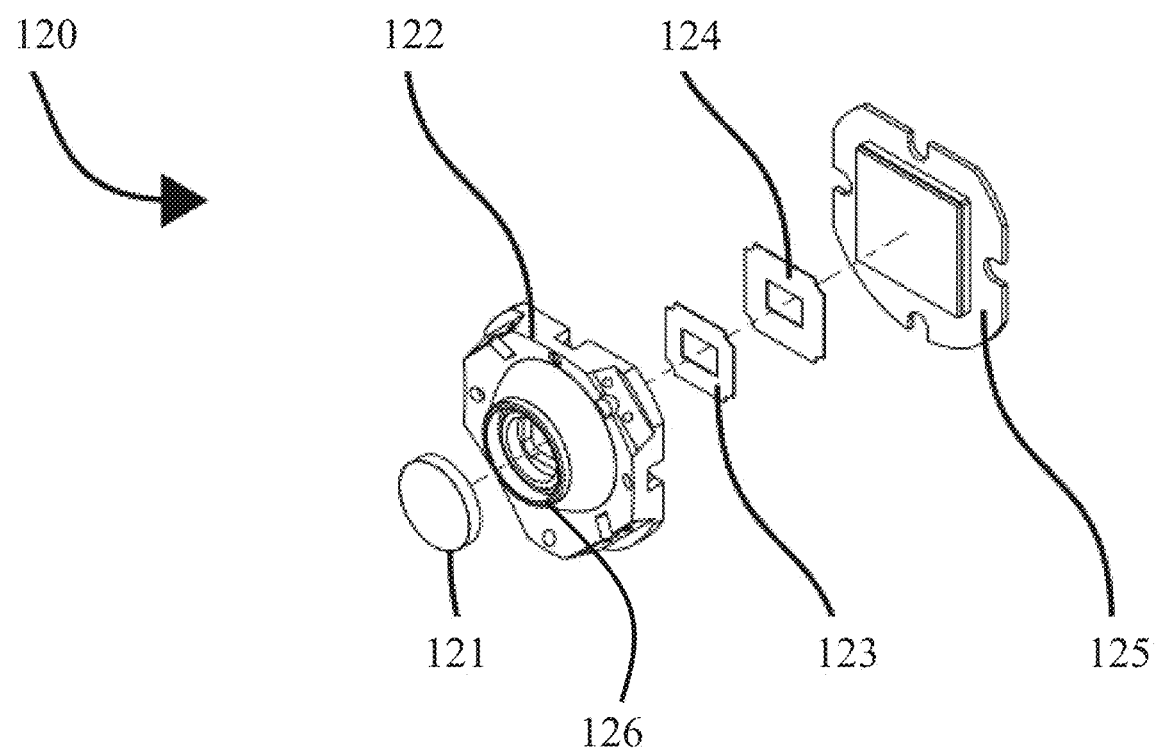
FIG. 1 shows an exploded view of a closed cavity sensor assembly according to an embodiment.

According to various embodiments, the adjustable sensor mounts described herein may comprise a closed cavity sensor assembly. This may keep dust and debris from reaching the surface of a sensor located within or enclosed by the sensor assembly, and may simplify a controlled clean room assembly process. FIG. 1 shows an exploded view of a variation of a sensor assembly 120 comprising a closed cavity according to an embodiment. The sensor assembly 120 may comprise a sensor/PCB assembly 125, which may be attached to or disposed or mounted on the base of a closed cavity platform 122. In some variations, the sensor/PCB assembly 125 may be bonded to or otherwise affixed to the base of the closed cavity platform 122. The closed cavity platform 122 may comprise a front port 126, which may be covered to form a sealed sensor compartment. In some variations, a window 121 may be bonded to or otherwise affixed to the front port 126 to complete the sealed sensor compartment. Other sensor assembly components may be located within the sealed sensor compartment. As shown in FIG. 1, for example, masks 123 and 124 may be located within the sealed sensor compartment. In some variations, the masks 123 and 124 may be placed within slots on closed cavity platform 122.

In some variations, the closed cavity sensor assemblies described herein may have a fixed distance between the front of the assembly (e.g., the window 121) and the sensor. It may be desirable for this distance to be as small as possible for compactness. However, contaminants on the outer window surface may have a larger effect when the distance between the window and the sensor/PCB assembly is smaller. Therefore, it may be desirable for the distance between the window and the sensor/PCB to be such that the sensor assembly is as compact as possible, while maintaining a desired image quality.

Figure 2:
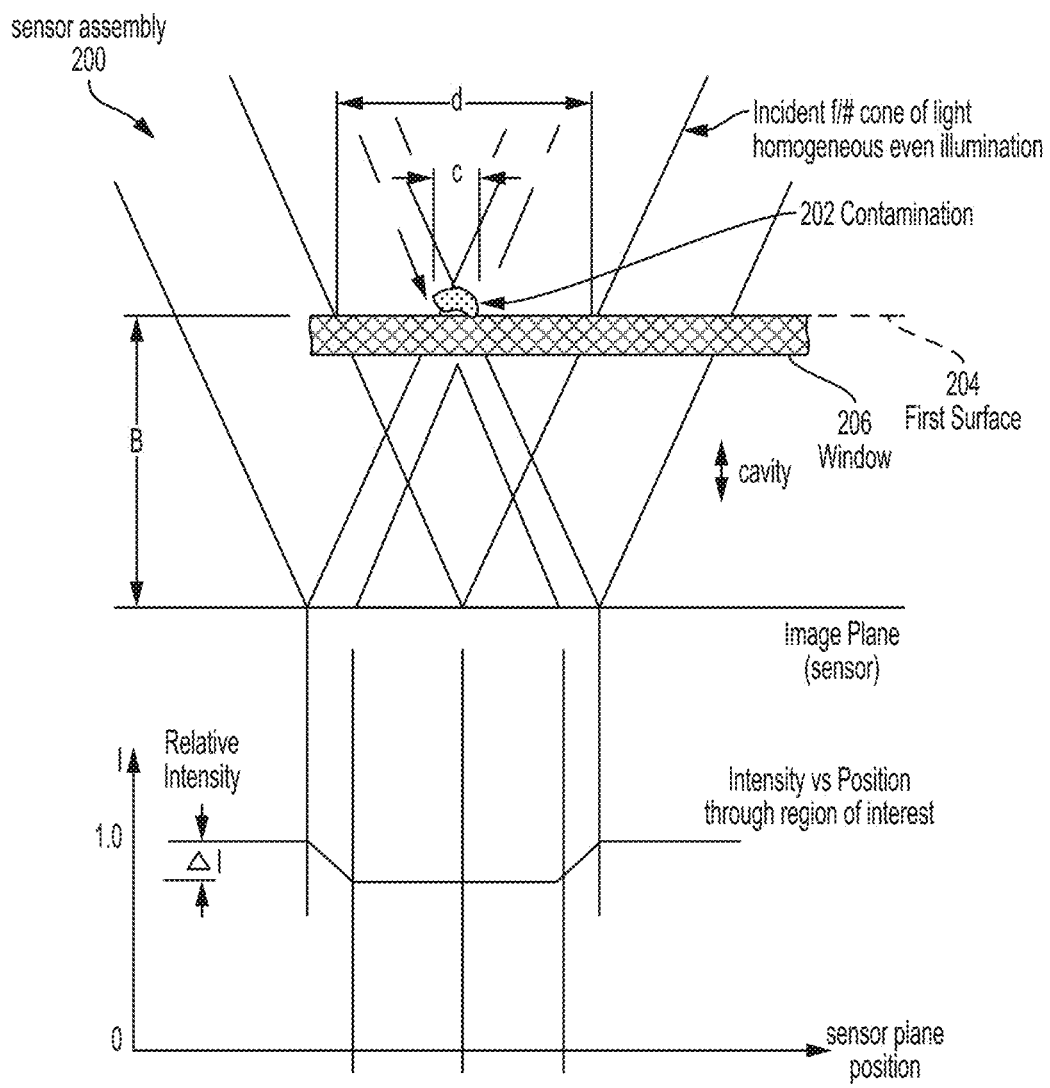
FIG. 2 shows the effect on image quality of contamination on a surface of a closed cavity sensor assembly according to an embodiment.

FIG. 2 is a diagram illustrating the effect of contamination on a surface of a sensor assembly on image quality according to an embodiment. More specifically, FIG. 2 shows a diagram of the spatial extent and magnitude of illumination intensity reduction imparted by a piece of contaminant partially obstructing light from falling on a sensor. Shown there is an illustration of a cross-section of a closed sensor assembly 200, with contaminant 202 located on a first surface 204 of a window 206 that blocks a portion of the incident light. The resultant illumination at the sensor may thus be lower in the penumbra region.

In order to facilitate maintaining optical performance, it may be desirable, in some variations, that the illumination profile not diminish by more than about 10% at any location on the sensor. In other variations, it may be desirable that the illumination profile not diminish by more than about 5% over the central 50% of the field of view of the sensor. The shape of the contaminant may affect the magnitude of illumination intensity reduction. For instance, when front-lit with uniform intensity light at a known f-number, the drop in illumination intensity for a spherical-shaped particle having a diameter c may be equal to:

$$\Delta I_{sphere} = \left(\frac{c*(f \text{ number})}{B}\right)^2$$

where B is the distance between the first surface 204 of the window 206 and the sensor. When the particle is a flat and thin object, such as a piece of lint, the magnitude of illumination intensity reduction may be greater. The drop in illumination intensity due to a flat and thin particle having a width of c may be equal to $$\Delta I_{flat} = \frac{c*(f \text{ number})}{B}$$

and thus, it may be desirable that the minimum distance between the first surface 204 of the window 206 be $$B = \frac{c}{\Delta I_{flat}} * (f \text{ number}).$$

Conversely, the clean room requirement may be that the maximum contaminant size is $$c = \frac{B * \Delta I_{flat}}{f \text{ number}}.$$

For example, in some variations it may be desirable for a closed cavity sensor assembly to be insensitive to contamination having a width less than or about 50 microns. If an f/8 incidence beam is used, and the minimum distance between the window and the sensor may be about 8 mm, assuming that changes in the modulation transfer function of the imaging system of less than about 0.05% are just barely observable.

The closed cavity sensor assemblies described herein according to the various embodiments may be part of adjustable sensor mounts, which may allow for or facilitate precise adjustment of sensor orientation in an imaging device/system. In some variations, the closed cavity sensor assemblies may be adjustably supported on (e.g., affixed to) a platform. Using adjustment fasteners (e.g., screws) or alignment adjustment jigs as described herein in exemplary variations, the orientation of the sensor assembly may be adjusted relative to the platform to precisely align the sensor of the sensor assembly with an optical axis of an imaging device. The closed cavity sensor assemblies may also be configured to be permanently or reversibly fixed after alignment, as described herein. The adjustment fasteners (e.g., screws), jigs, or the like may be removed from the sensor mounts after alignment, and the sensor assembly may be separately fixed. In various embodiments, having separate mechanisms for alignment and fixation may allow for more precise alignment, greater alignment stability, and/or more compact designs.

FIGS. 3A, 3B, and 3C-3D show exploded, front, and section views, respectively, of variation of an adjustable sensor mount 310 according to an embodiment. As shown there, the adjustable sensor mount 310 may comprise a sensor assembly 320 and a platform 330, which may be adjustably attached via a spherical joint allowing for tilt adjustment. The sensor assembly 320, which may be a closed cavity sensor assembly as described with respect to FIG. 1, may comprise, for example, a curved, convex surface. This surface may have a corresponding and complementary shape to a surface of the platform 330 (e.g., a curved, concave surface of the platform 330). In some variations, the sensor assembly may comprise a concave surface and the platform may comprise a convex surface, or they may feature any suitable interfacing surfaces that may facilitate movement relative to each other in a finely adjustable manner. The platform 330 may be configured to be fastened to a carriage or frame of an imaging device/system. For example, the platform 330 may comprise centering elements (e.g., holes 332) that may be used to center and fasten the platform 330 to the carriage or frame of an imaging device/system. In some embodiments, adjustable sensor mount 310 may include window 321.

The sensor assembly 320 may be fastened to the platform 330 using, for example, a plurality of adjustment fasteners (e.g. screws 340), tension fasteners (e.g., screws 341), springs 342, kinematic balls 344, and/or kinematic slotted ball nuts 346. The kinematic balls 344 and ball nuts 346 may be disposed in indentations (e.g., 60 degree conical indentations) set into the closed cavity platform 322 and the platform 330. After initial assembly during which the sensor assembly 320 is fastened to the platform 330, tightening and/or loosening of one or more fasteners (e.g., screws) may cause movement of the curved, convex surface of the sensor assembly 320 within the curved, concave surface of the platform 330, thus allowing for fine adjustment of the sensor orientation. In some variations, the adjustable sensor mount 310 may be configured such that tightening and/or loosening of the screws may cause rotation of the sensor about its center by moving portions of the sensor assembly 320 toward and away from the platform 330.

Certain variations of the adjustable sensor mount systems according to various embodiments may be configured for finer resolution adjustment. For example, screws with finer pitch differential may allow for finer adjustment resolution. As another example, locating the adjustment screws 340 and adjustment tension screws 341 further from the center of the adjustable sensor mount 310 (e.g., further from the center of the sensor) may allow for increased adjustment resolution, since each turn of a screw may result in a smaller change in the relative position of the sensor assembly 320 and the platform 330, and thus in a smaller change in the angle of alignment of the sensor. In some variations, the fasteners may be located further from the center of the adjustable sensor mount by attaching the adjustable sensor mount to an extension jig.

In addition to being configured for tilt adjustment, in some variations adjustable sensor mount systems may be configured for translational alignment. For example, adjustable sensor mount 310 may be mounted to allow for x-y linear translation and/or translation along the optical axis, such as by mounting to an x-y linear translation stage. In some variations, the x-y stage may be adjustable by integrated micrometers. In some variations, the adjustable sensor mount 310 may be mounted to facilitate movement along the optical axis (e.g., mounted onto a guiderail that allows for movement along the optical axis, or when the adjustable sensor 310 is mounted onto an x-y stage, the x-y stage may be mounted onto a guiderail that allows for movement along the optical axis).

The adjustable sensor mount systems described herein according to the various embodiments may be configured such that after the sensor (e.g., as part of a sensor/PCB assembly) is properly aligned, the sensor may be fixed in the aligned position. For example, referring to the example of FIGS. 3A-3F, following adjustment of the tilt of the sensor assembly 320 (e.g., alignment of the sensor with an imaging optical axis), the sensor assembly 320 may be fixed in a particular alignment relative to the platform 330. In some variations, the sensor assembly 320 may be reversibly fixed to the platform 330. For example, the sensor assembly 320 may be reversibly fixed to the platform 330 by securing the closed cavity platform 322 to the platform 330 with one or more bridge assemblies. The one or more bridge assemblies may attach to both the closed cavity platform 322 and the platform 330 in order to fix their relative positions and prevent further tilt adjustment of the sensor assembly 320.

Figure 3A:
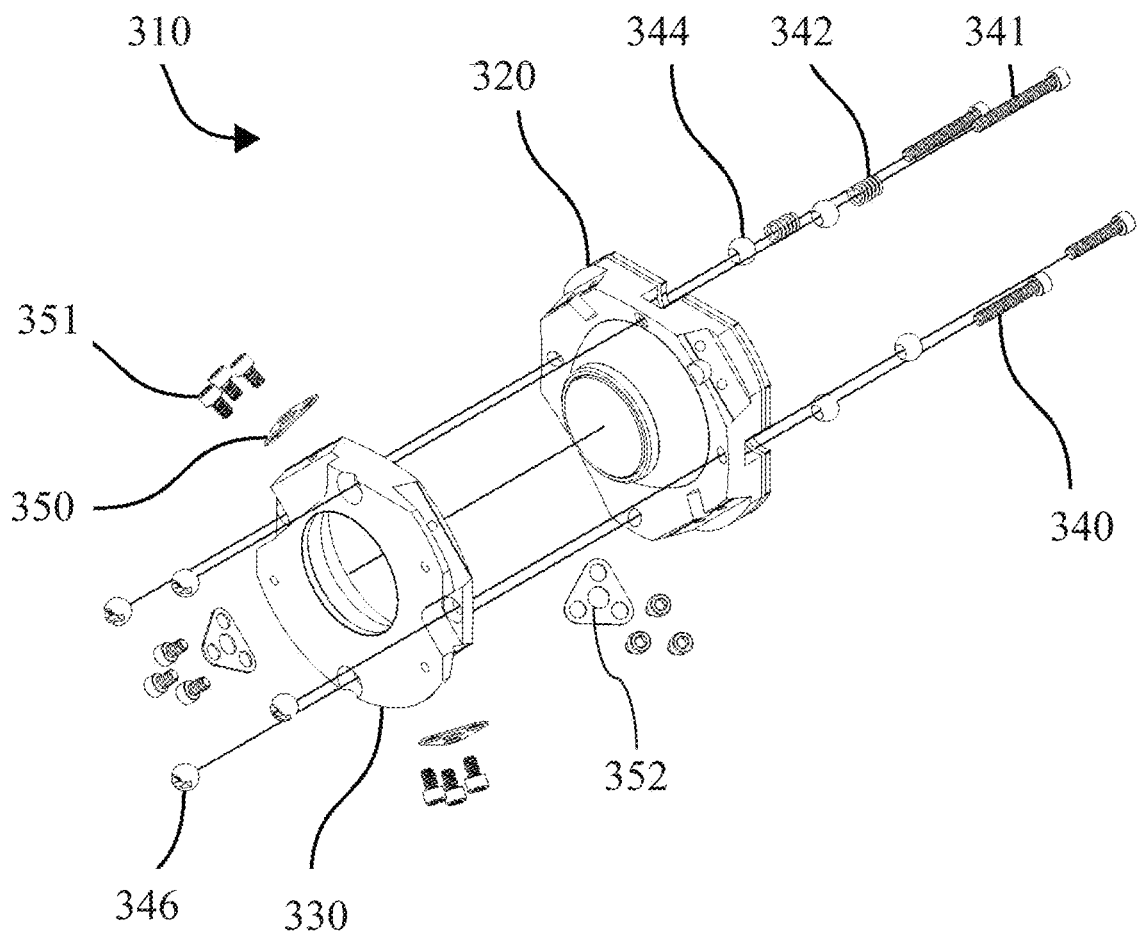
FIGS. 3A, 3B, and 3C-3D show exploded, front, and section views, respectively, of an adjustable sensor mount according to an embodiment.
Figure 3B:
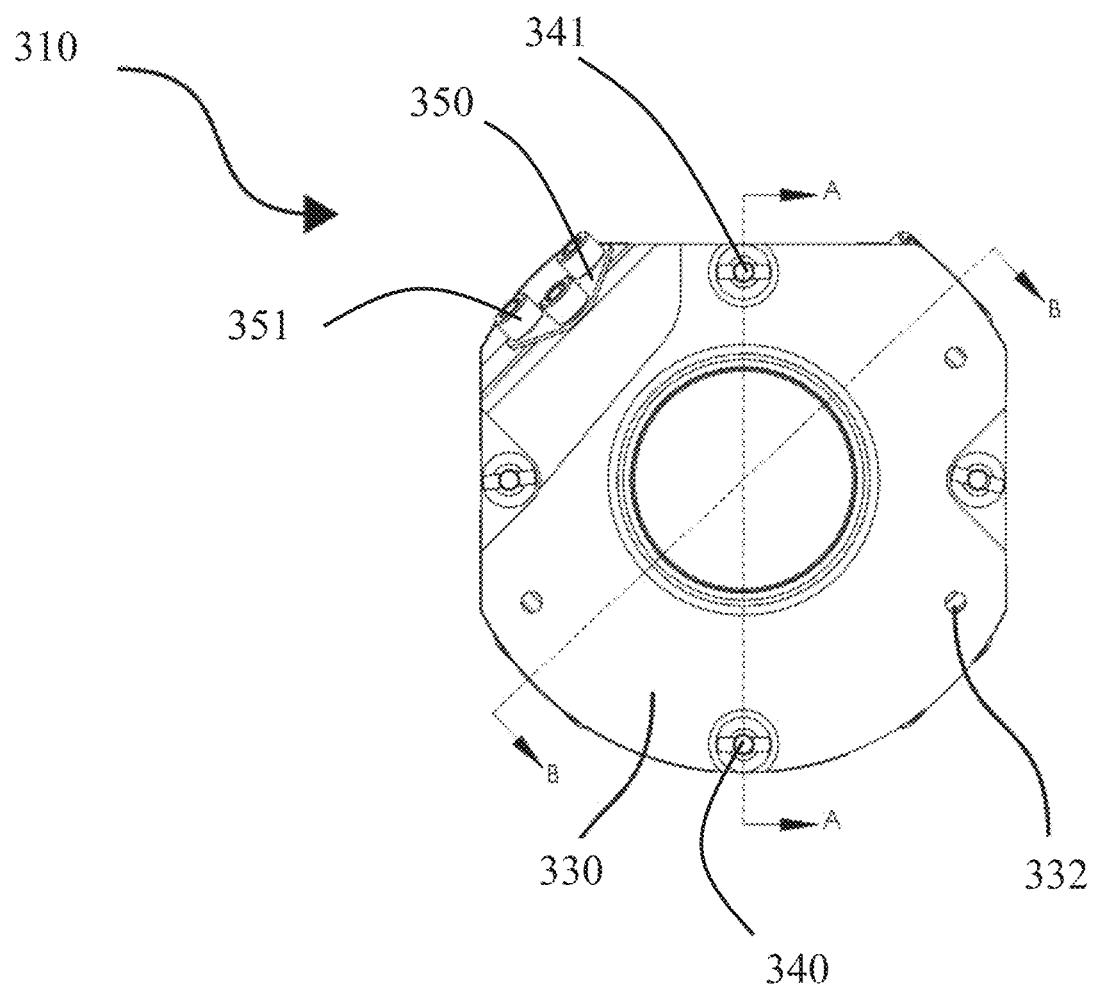
Figure 3C:
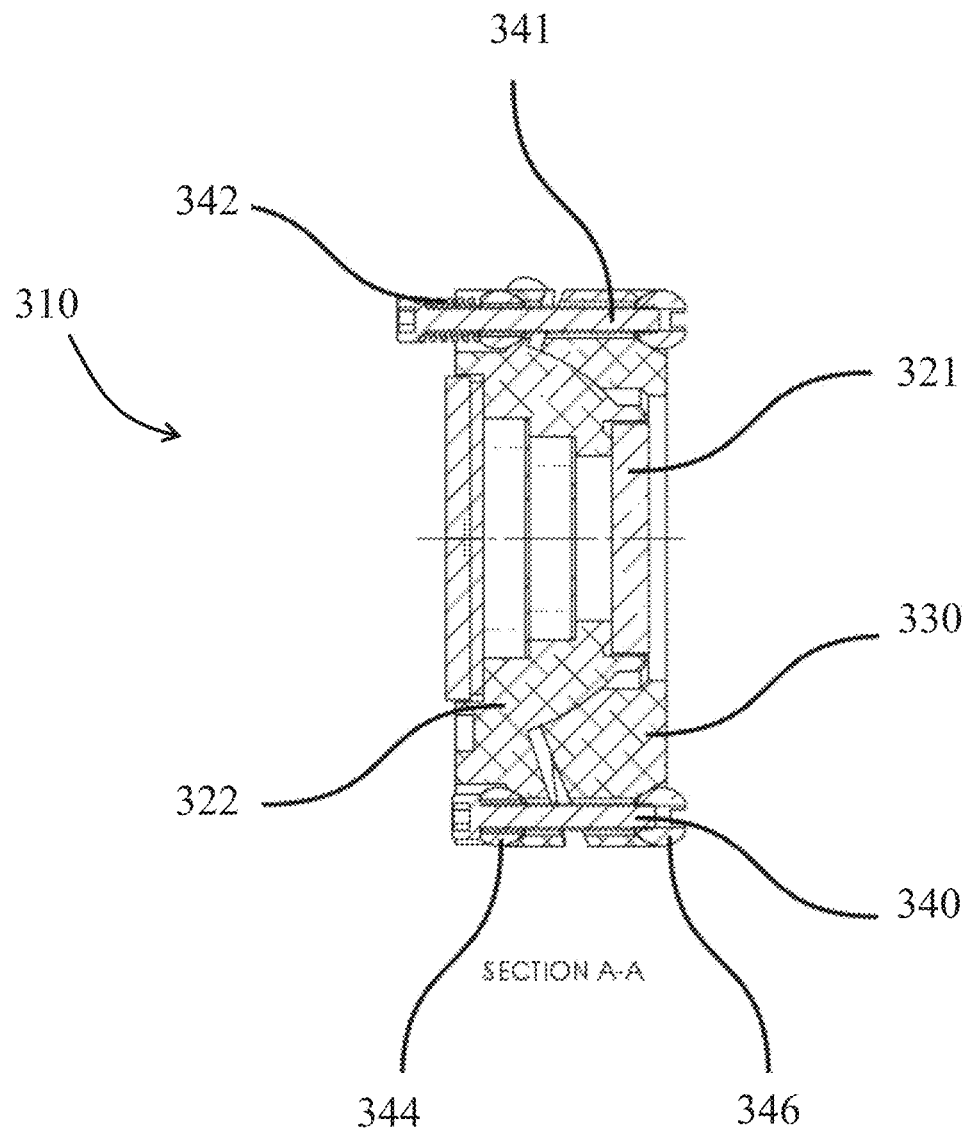
Figure 3D:
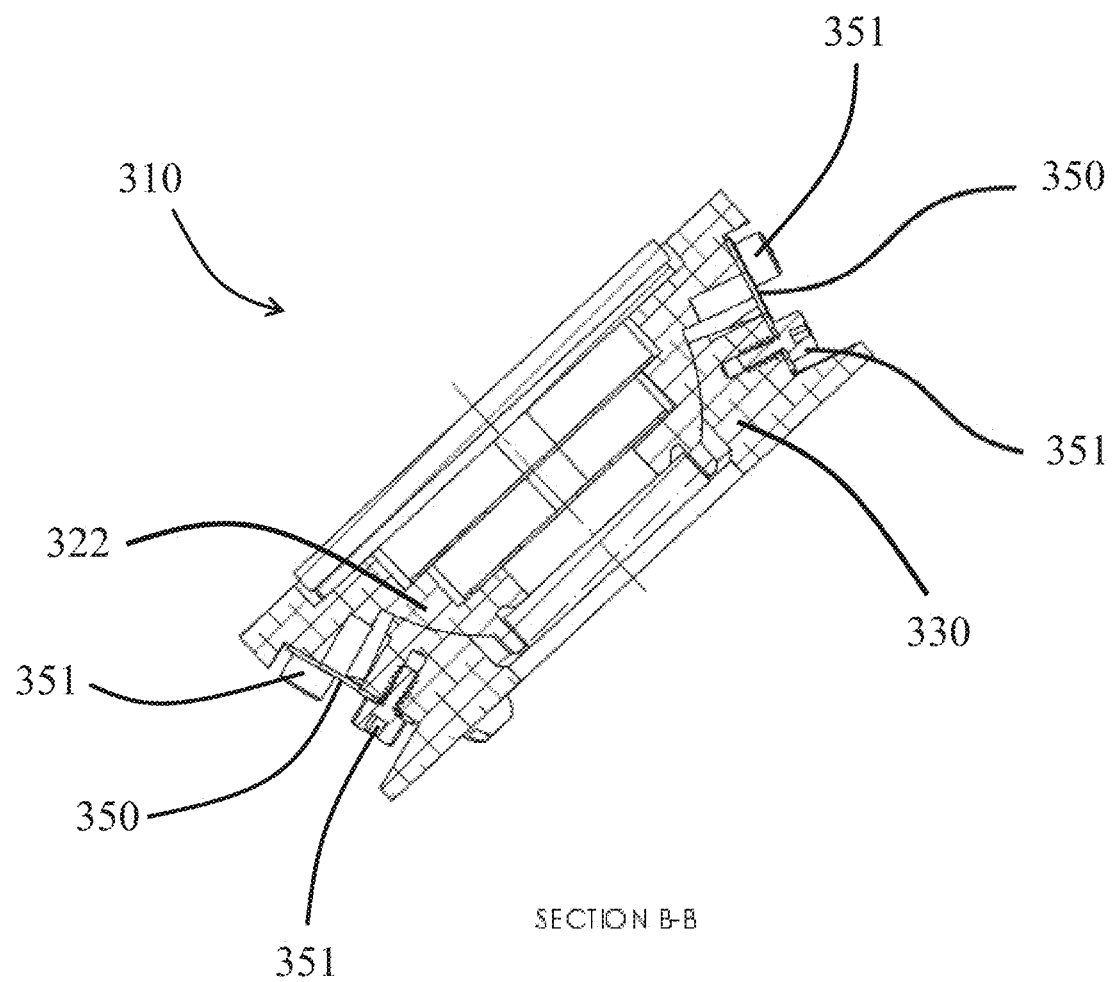

In some variations, the bridge assemblies may comprise bridge plates 350 and bridge plate fasteners (e.g. bridge plate screws 351). For example, each bridge plate 350 may be secured by one or more bridge plate screws 351 to each of the sensor assembly 320 and the platform 330. As shown in FIG. 3D, two bridge plates 350 may be disposed at opposite sides of a secured adjustable sensor mount 310. Each bridge plate 350 may be attached to both the platform 330 and the closed cavity platform 322 via bridge plate fasteners (e.g., bridge plate screws 351), and may be positioned so that a normal vector passing through the center of the bridge plate's screw hole (openings) pattern also passes through the center of the image plane. The bridge plates 350 may comprise holes larger than the diameter of the corresponding bridge plate screws 351 to accommodate the adjustable range of tilt of the sensor assembly 320. In some variations, the bridge assembly may maintain alignment of the sensor, while optionally allowing for readjustment by removal of the bridge assembly (e.g., for servicing).

Figure 3E:
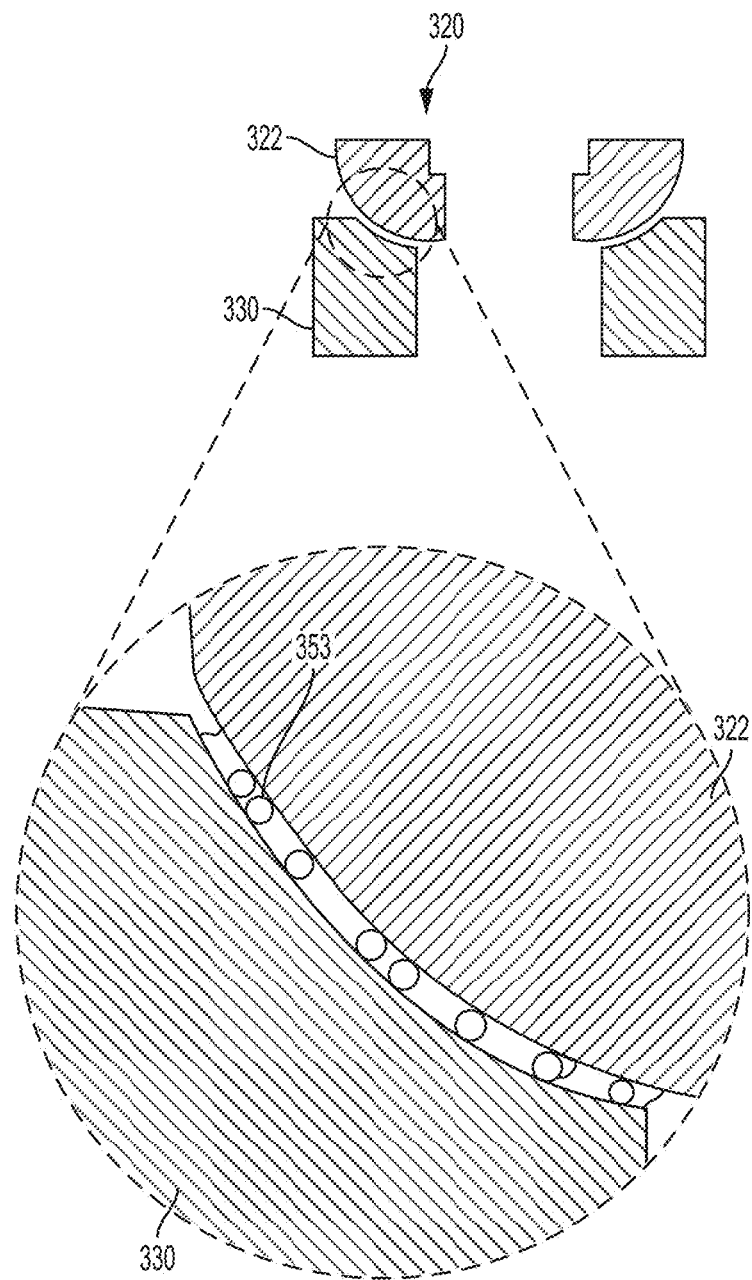
FIG. 3E illustrates a close-up view of a portion the sensor assembly where the closed cavity platform is fixed to the platform using bonding glue according to an embodiment.
Figure 3F:
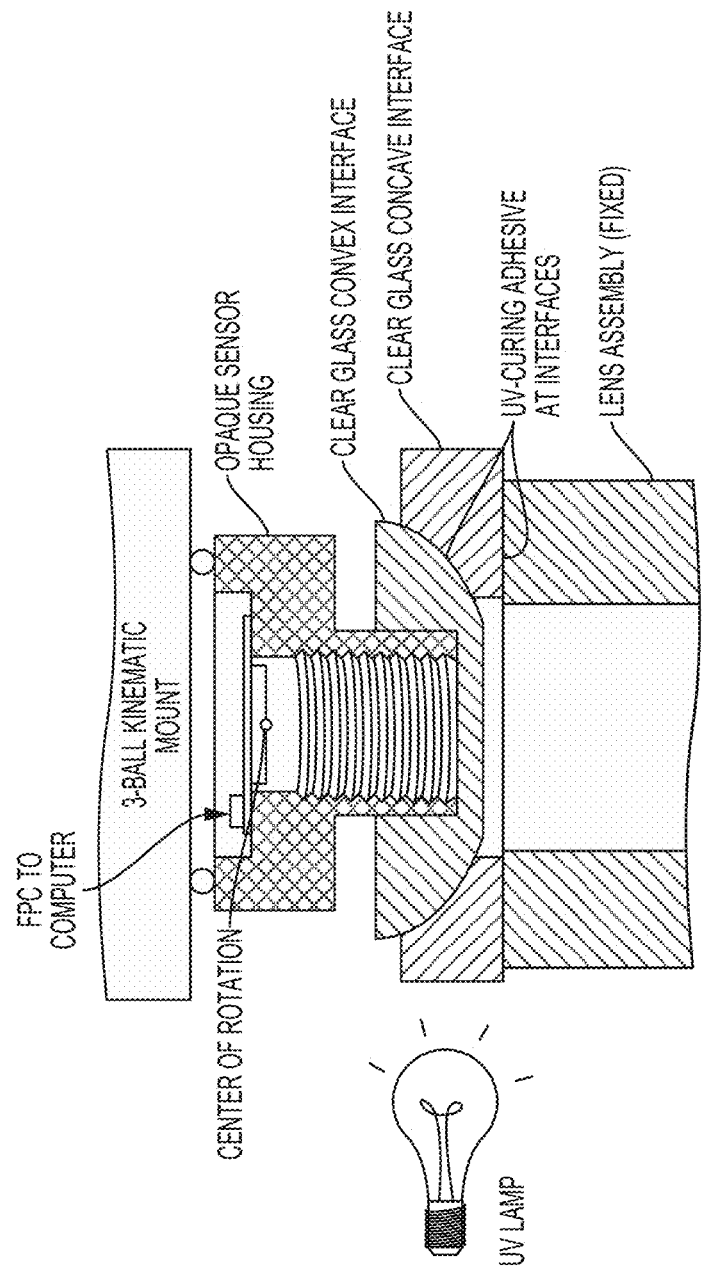
FIG. 3F shows an adjustable sensor mount made of a UV-transmitting material according to an embodiment.

The sensor assembly may in some variations be permanently fixed after alignment. For example, the sensor assembly may be permanently fixed to the platform by application of bonding glue between the joint surfaces. Bonding may be performed using any suitable bonding agent or technique such as, for example, using glue, epoxy, light activated glue, cold welding, electro-soldering or a combination thereof. FIG. 3E illustrates a close-up view of a portion of a variation of the sensor assembly 320 where the closed cavity platform 322 is fixed to the platform 330 using bonding glue. As shown there, in some variations, the bonding agent (e.g., glue) may comprise fixed-diameter beads 353, which may maintain an invariant bond gap between the joint surfaces such that the bond gap is constant independent of steering/alignment of the sensor assembly 320. It should be appreciated that bonding glue or other boding agent may be used alone for fixation, or in conjunction with other fixation methods, such as, for example, bridge plates and screws or other fasteners, as described herein. As shown in FIG. 3E, in some variations the bonding may be performed such that a bond gap is substantially normal to a radial line that passes through the center of the image plane, which may require that the bonded components, such as closed cavity platform 322 and platform 330, have similar or equivalent coefficients of thermal expansion. In some such variations, a bonding agent may be used and may function as a lubricant between the surfaces of closed cavity platform 322 and platform 330 during alignment. In some variations, bonding may be performed additionally, or alternatively, such that a bond gap is not substantially normal to a radial that passes through the center of the image plane. For example, bonding may be performed to bond closed cavity platform 322 and platform 330 near the location of bridge plates 350, such as by applying a bonding agent through bridge plate port 352. In some such variations, the bond may be capable of being split after bonding to facilitate realignment, if necessary.

In some variations in which a sensor assembly is fixed to the platform using bonding glue or another bonding agent, the bonding glue or bonding agent may be light activated. For example, components of the sensor assembly and/or platform may be made of a UV-transmitting material (e.g., glass), and the bonding glue or bonding agent may be a Ultraviolet (UV)-activated glue/agent, as shown for example in FIG. 3F. In these variations, Ultraviolet (UV) light may be delivered to the bonding glue/agent through the material of the sensor assembly and/or platform. This may allow for a shorter bond curing time.

Figure 4A:
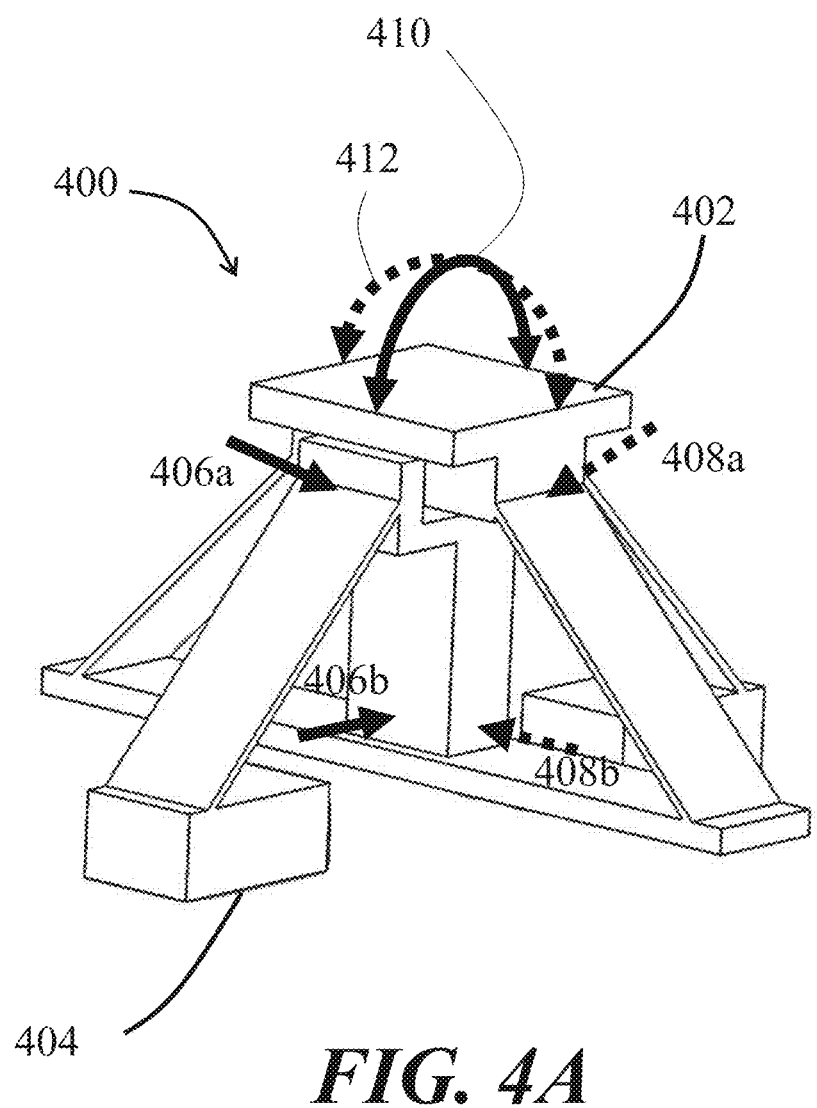
FIGS. 4A-4B show perspective views of a flexure assembly according to an embodiment.
Figure 4B:
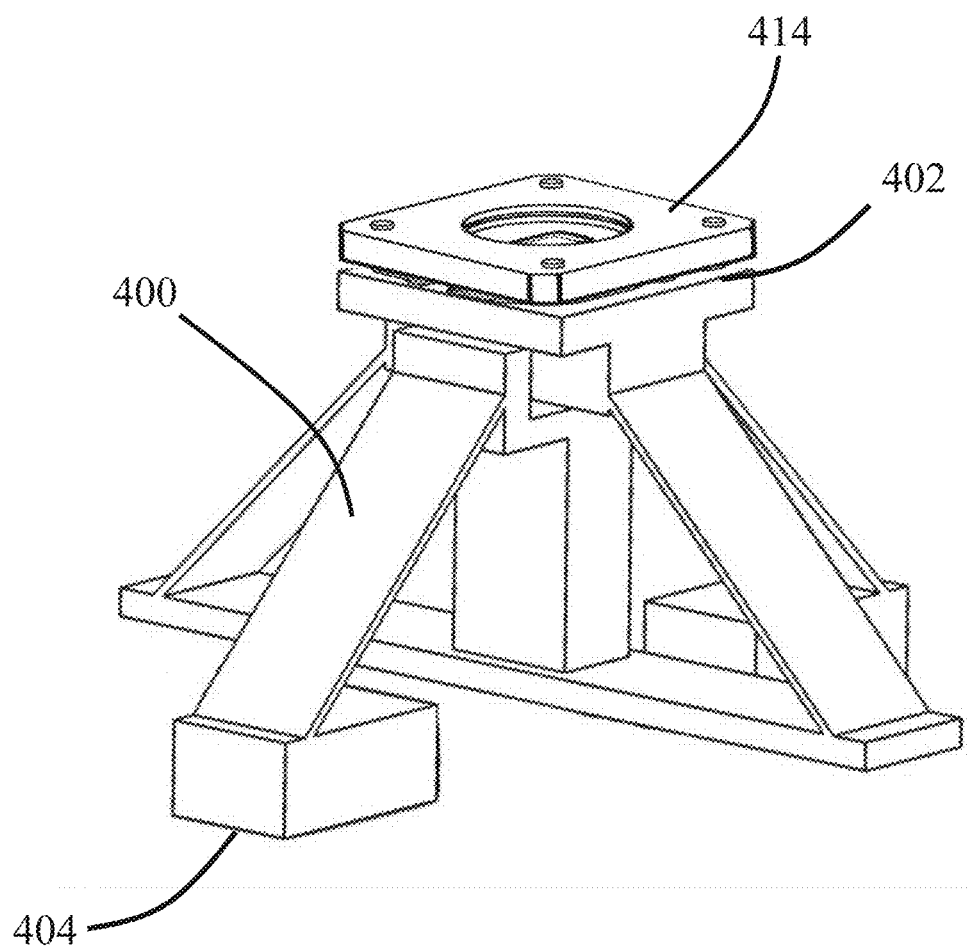

In other variations of adjustable sensor mount systems, a flexure assembly may be used instead of a spherical joint to provide sensor tilt adjustment. FIGS. 4A-4B show perspective views of an exemplary flexure assembly 400 that may allow for sensor tilt adjustment in two axes. The tilt of the top sensor mount plane 402 of the flexure assembly 400 may be adjusted by adjustment screws against the side of each flexure component. As shown in FIG. 4A, according to an embodiment, the top sensor mount plane 402 of the flexure assembly 400 may be tilted (represented by double-headed arrow 410) about a first axis by applying force at point 406a, and tilted (represented by double-headed arrow 412) about a second axis by applying force at point 408a, with force application that may be directed normal to a thin flexure blade to facilitate prevention of undesired parasitic motion in degrees of freedom other than rotation about the desired tilt axis. Additionally, or alternatively, the top sensor mount plane 402 of the flexure assembly 400 may be tilted (represented by double-headed arrow 410) about a first axis by applying force at point 406b, and tilted (represented by double-headed arrow 412) about a second axis by applying force at point 408b. Such force may be applied, for example, by adjustment fasteners (e.g., screws) against the side of each flexure component. This may impart smooth flexure deformations to rotate the top sensor mount plane 402. Such a design may avoid stick-slip motion (which may occur, for example, between joint surfaces), and thus may allow for/facilitate smoother motion control when making very fine alignment adjustments. As shown in FIG. 4B, a top-mounted closed cavity sensor mount 414 may be mounted to the top sensor mount plane 402 of the flexure assembly 400 to allow for alignment adjustment of the sensor. The bottom surfaces 404 of the flexure assembly 400 may be mounted to a rigid frame.

Figure 5A:
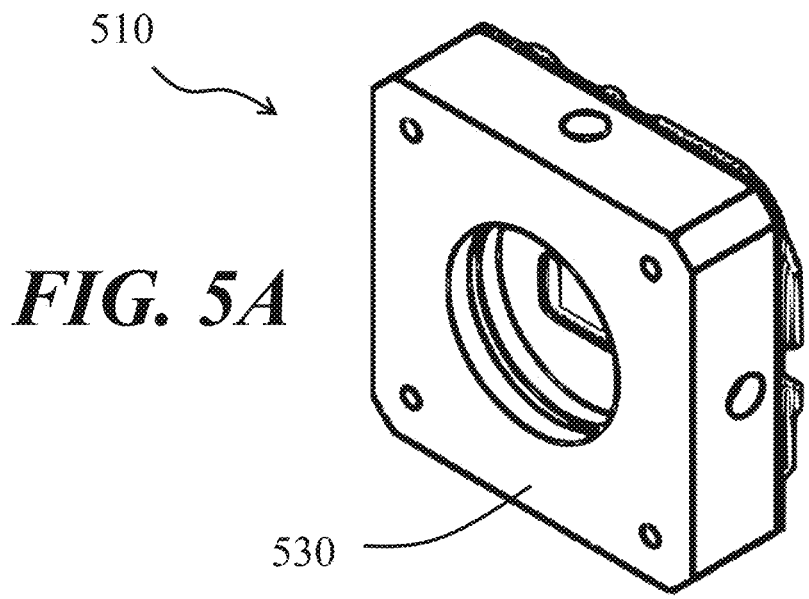
FIGS. 5A-5C show an exemplary adjustable sensor mount configured to be adjusted using a flexure plate according to an embodiment.
Figure 5B:
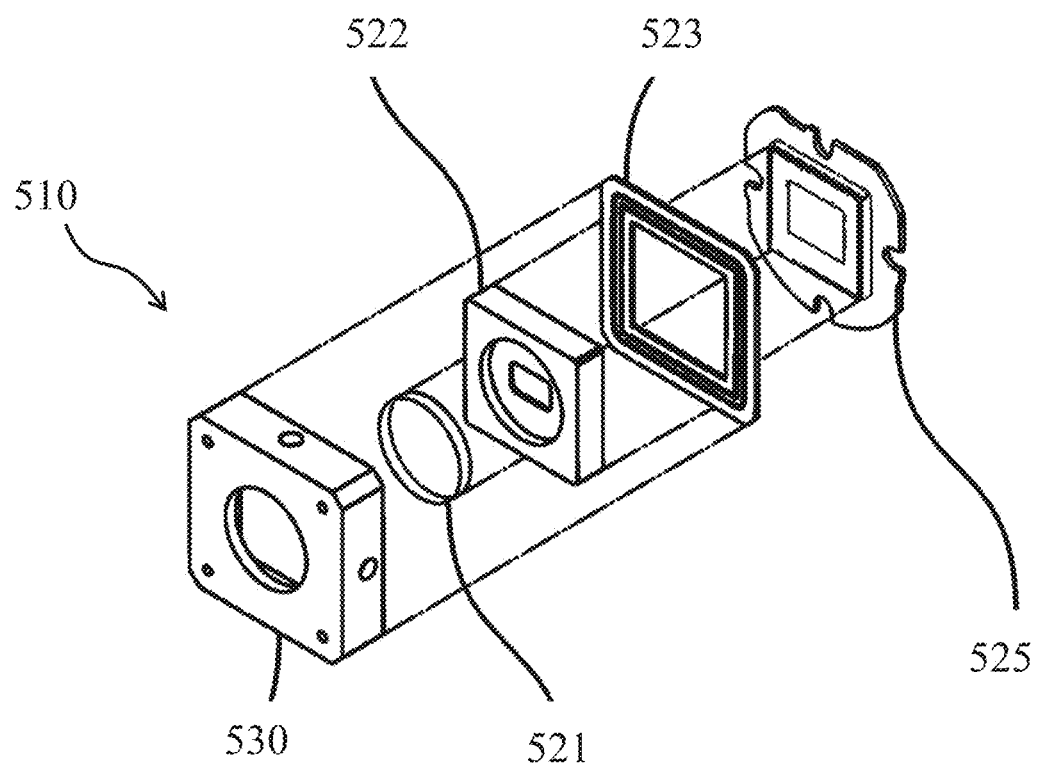
Figure 5C:
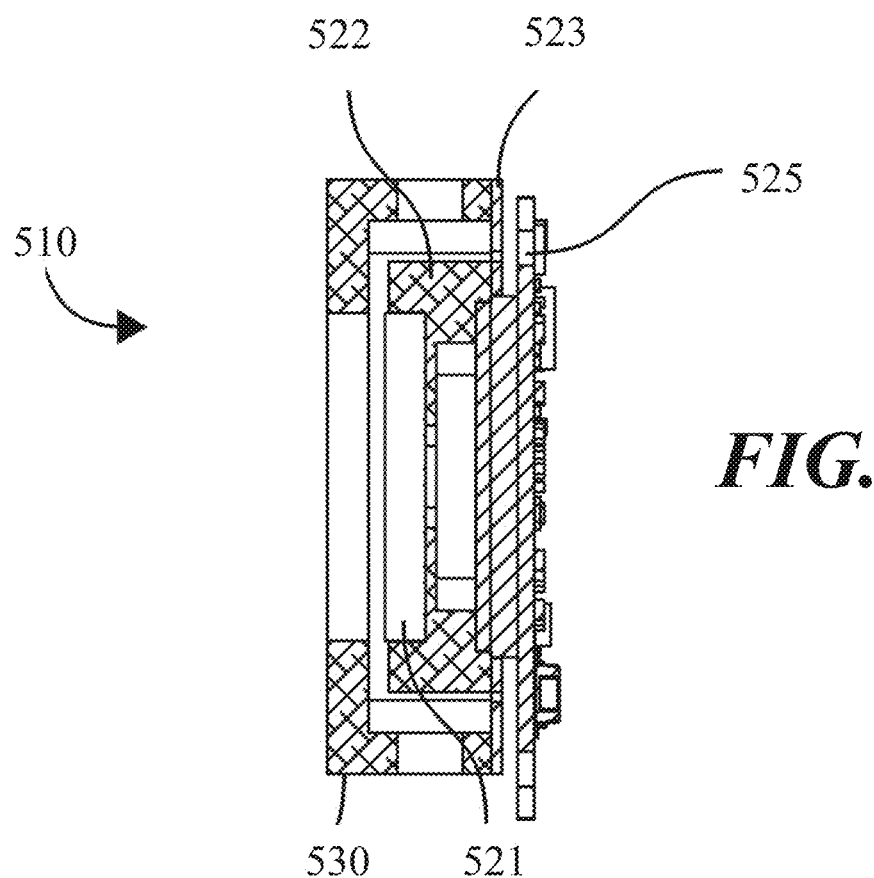
Figure 5D:
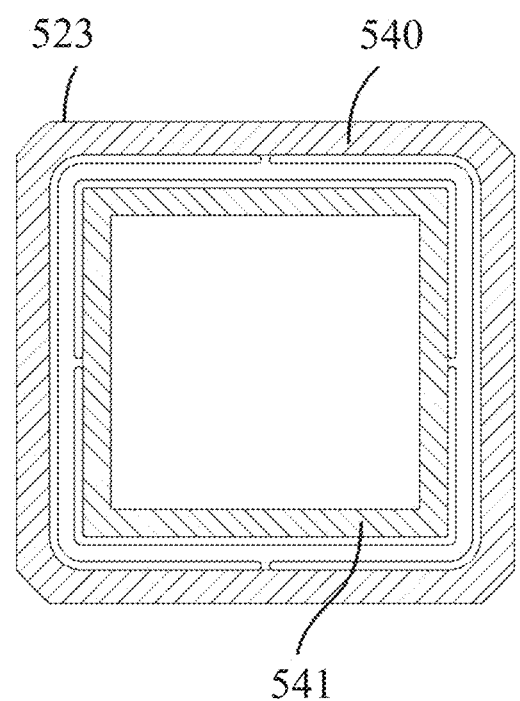
FIGS. 5D-5F show the flexure plate alone according to an embodiment.
Figure 5E:
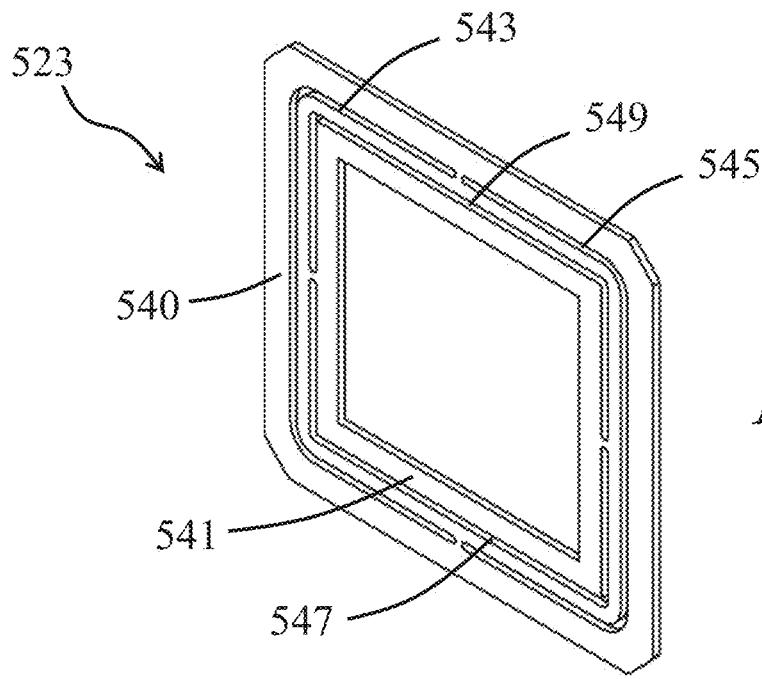
Figure 5F:
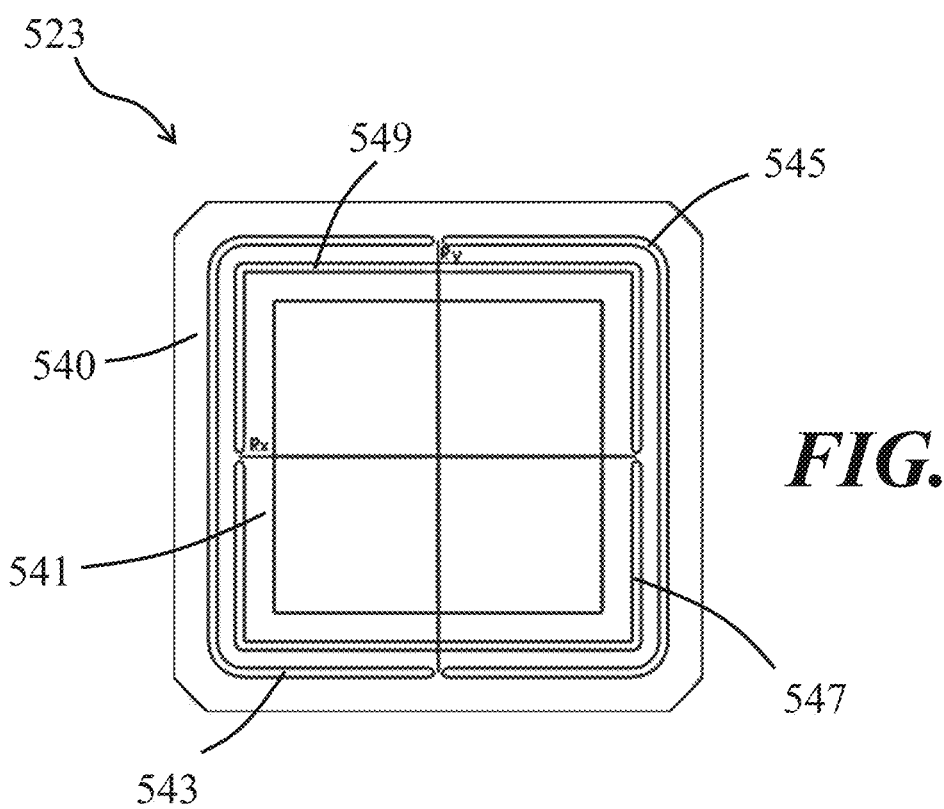

FIGS. 5A-5C show an exemplary adjustable sensor mount system configured to be adjusted using a flexure plate. As best shown in the exploded view of FIG. 5B and the cross-sectional view of FIG. 5C, the adjustable sensor mount 510 may comprise a flexure plate 523, an X-Y platform 530, a closed cavity platform 522 comprising a window 521, and a sensor/PCB assembly 525. FIGS. 5D-5F show the flexure plate 523. The X-Y platform 530 may be bonded to an outer region 540 of the flexure plate 523, and the closed cavity platform 522 may be bonded to an inner region 541 on the flexure plate 523. The outer edges of the window 521 overlying the sensor assembly 525 may be bonded to the closed cavity platform 522.

The flexure plate 523 may allow the sensor/PCB assembly 525 to be tilted about the x and/or y axes of the sensor, while the X-Y platform 530 may allow the sensor/PCB assembly to be translated along the x and/or y axes of the sensor. During alignment, the tilt of the flexure plate 523 may be adjusted by applying rotations to the sensor/PCB assembly 525 about the sensor plane using an alignment jig as described herein. The inner region 541 of the flexure plate 523 may be rotated about the x and y axes relative to the outer region 540, through torsional deformation at connection points between channels 543, 545, 547, 549 in the flexure plate 523. Translations may be applied to the entire adjustable sensor mount 510 by translating the X-Y platform 530.

After alignment of the sensor/PCB assembly 525, the tilt and/or translational alignment of the sensor may be fixed. For example, the tilt may be permanently set by applying potting glue inside the X-Y platform 530 to fix the closed cavity platform 522 relative to the X-Y platform 530.

Figure 6A:
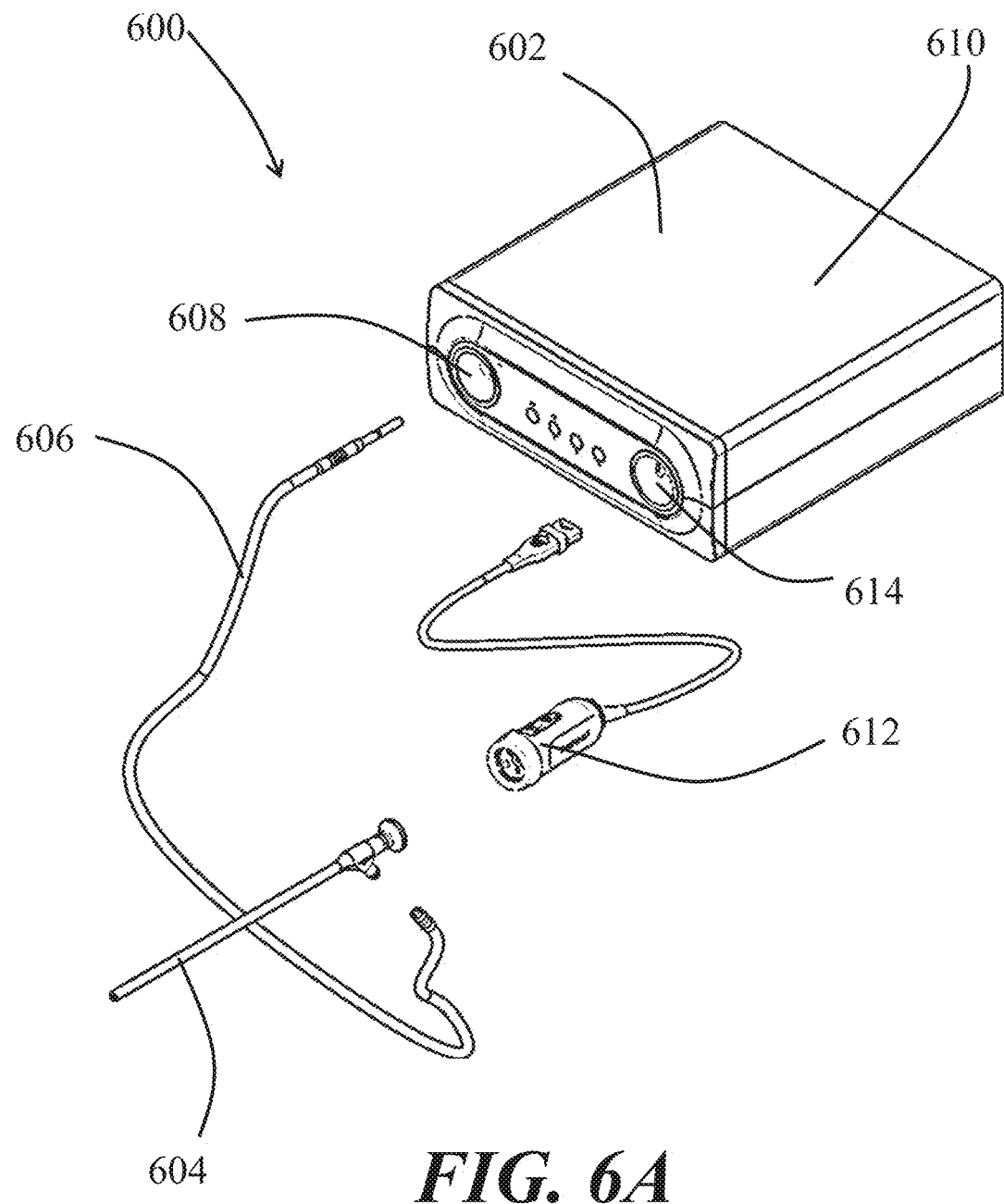
FIG. 6A shows a variation of an endoscopic imaging system comprising an adjustable sensor mount according to an embodiment.

One or more of the adjustable sensor mount systems described herein may be a component of various types of imaging systems. In some variations, an adjustable sensor mount system may be a component of an endoscopic imaging system, such as but not limited to an endoscopic fluorescence imaging system. FIG. 6A shows an example of an endoscopic imaging system 600 that may comprise an adjustable sensor mount as described herein. Imaging system 600 may comprise an illuminator 602 with a light source assembly configured to provide visible light and/or fluorescence excitation light to a surgical laparoscope 604 via a light guide 606 that is connected to the illuminator 602 via a light guide port 608. A processor 610 and/or controller 620 may, in some variations, be within the same housing as the illuminator 602, as shown in FIG. 6A. An image acquisition assembly 612 may receive signals via connection to the laparoscope 604, and may pass acquired images to the processor 610 via connection to the processor such as through port 614. The imaging system 600 may also comprise one or more displays (e.g., computer screen or other monitor), or any suitable systems for communicating and/or storing images and image-related data.

Figure 6B:
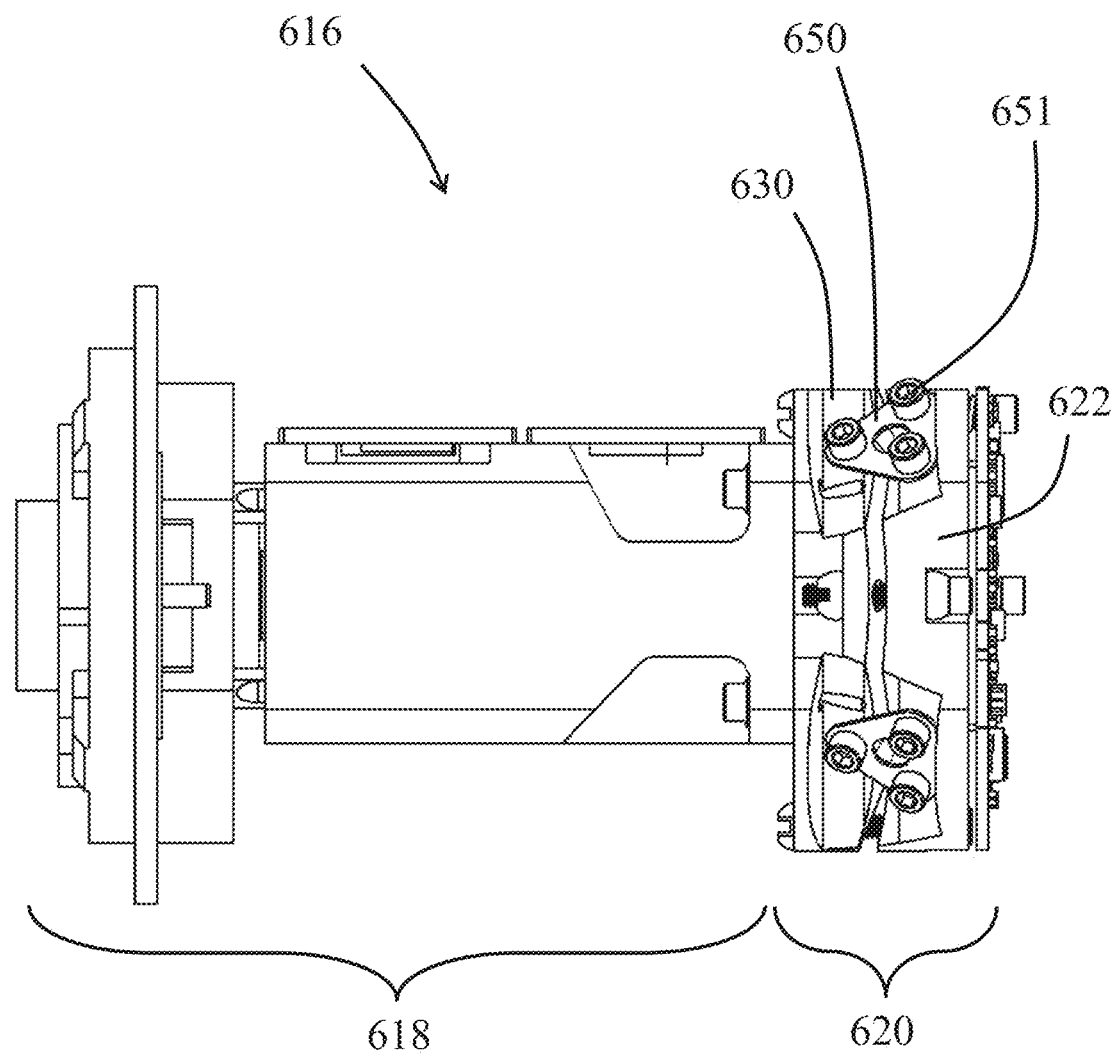
FIG. 6B shows a portion of the endoscopic imaging system of FIG. 6A.
Figure 6C:
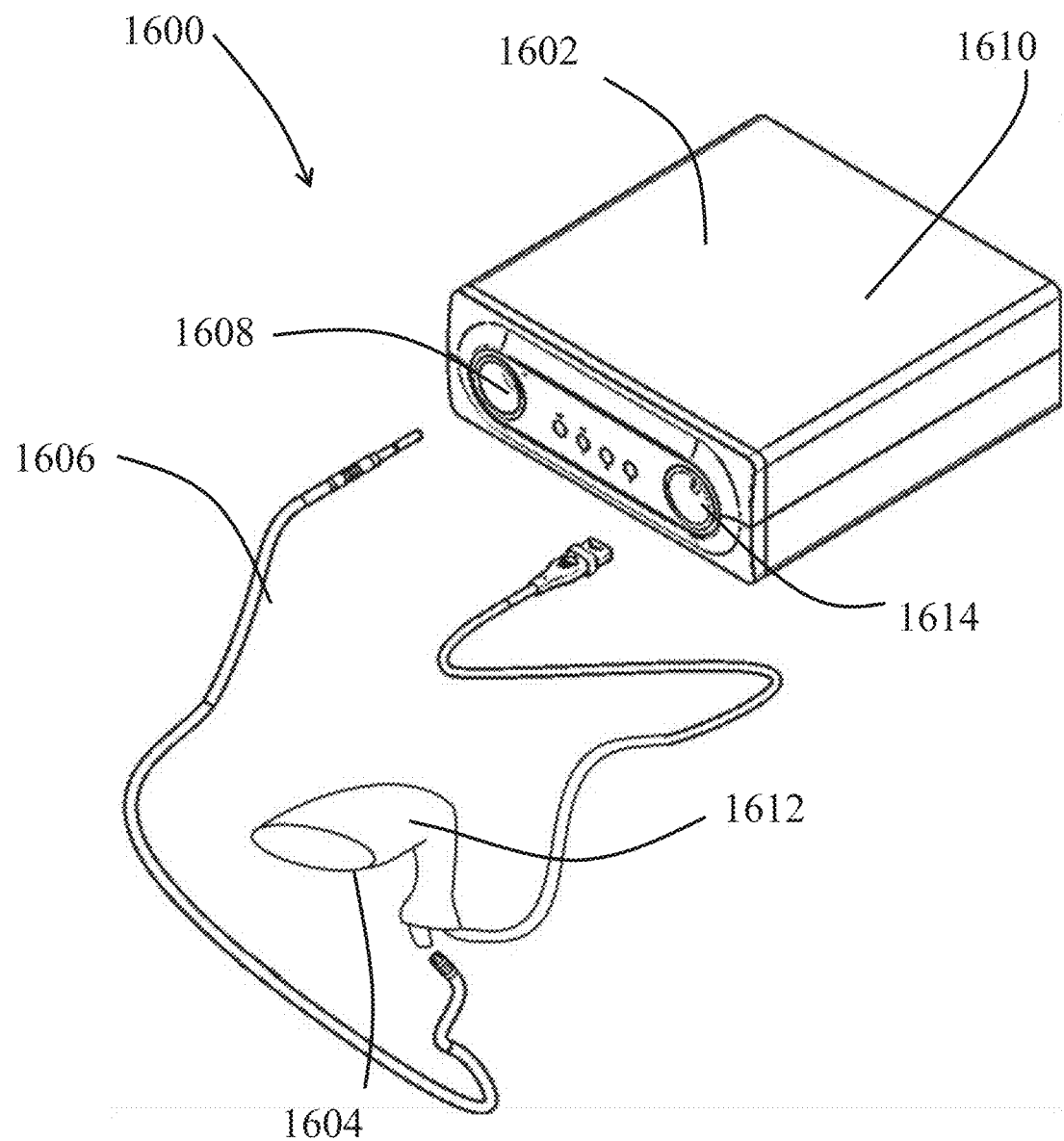
FIG. 6C shows a variation of an open field imaging system comprising an adjustable sensor mount according to an embodiment.

In some variations, an adjustable sensor mount system may be a component of an open field imaging system, such as but not limited to an open field fluorescence imaging system. FIG. 6C shows an example of an open field imaging system 1600 that may comprise an adjustable sensor mount as described herein. Imaging system 1600 may comprise an illuminator 1602 with a light source assembly configured to provide visible light and/or fluorescence excitation light to an open field imaging head 1604 via a light guide 1606 that is connected to the illuminator 1602 via a light guide port 1608. A processor 1610 and/or controller 1620 may, in some variations, be within the same housing as the illuminator 1602, as shown in FIG. 6C. Open field imaging head 1604 may comprise an image acquisition assembly 1612 which may receive signals and may pass acquired images to the processor 1610 via connection to the processor such as through port 1614. The imaging system 1600 may also comprise one or more displays (e.g., computer screen or other monitor), or any suitable systems for communicating and/or storing images and image-related data.

In variations in which the imaging system 600 (or 1600) is configured for fluorescence imaging alone or in combination with another imaging modality (e.g., white light imaging), the light source assembly 602 (or 1602) may be configured to provide fluorescence excitation light (e.g., near infrared (NIR) light) alone or in addition to visible light. For example, the light source assembly 602 (or 1602) may comprise a visible light source that emits visible light (e.g., full spectrum visible light) and an excitation light source that emits excitation light for exciting fluorophores in an object (e.g., tissue) and causing fluorescence emission.

In variations of the imaging system comprising a visible light source, the visible light source may be configured to emit visible light for illumination of the object (e.g., tissue) to be imaged. In some variations, the visible light source may include one or more solid state emitters, such as LEDs and/or laser diodes. For example, the visible light source may include blue, green, and red (or other color components) LEDs or laser diodes that in combination generate white light illumination. These color component light sources may be centered around the same wavelengths around which the image acquisition assembly (described further herein) is centered. For example, in variations in which the image acquisition assembly includes a single chip, single color image sensor having an RGB color filter array deposited on its pixels, the red, green, and blue light sources may be centered around the same wavelengths around which the RGB color filter array is centered.

In variations of the imaging system comprising an excitation light source, the excitation light source may be configured to emit excitation light suitable for exciting intrinsic (endogenous) fluorophores and/or extrinsic fluorophores (e.g., a fluorescence imaging agent introduced into the object) located in the object (e.g., tissue) being imaged. The excitation light source may include, for example, one or more LEDs, laser diodes, arc lamps, and/or illuminating technologies of sufficient intensity and appropriate wavelength to excite the fluorophores located in the object being imaged. For example, the excitation light source may be configured to emit light in the near-infrared (NIR) waveband (approximately 805 nm), though other excitation light wavelengths may be appropriate depending on the application.

One or more of the light sources of the light source assembly 602 (or 1602) may be operated in a pulsed mode during the image acquisition process according to a timing scheme. For example, when the excitation light source comprises a laser diode, power to the laser diode may be provided by, for example, a high-current laser driver, which may optionally be operated in a pulsed mode during the image acquisition process according to a timing scheme.

In some variations, the light source assembly 602 (or 1602) may further comprise one or more optical elements that shape and/or guide the light output. The optical components may include one or more lenses, mirrors (e.g., dichroic mirrors), light guides and/or diffractive element. For example, the output from a laser diode may be passed through one or more focusing lenses, and then through a light guide. The light may be further passed through an optical diffractive element (e.g., one or more optical diffusers). An optical sensor such as a solid state photodiode may be incorporated into the light source assembly and may sample the illumination intensity produced by one or more of the light sources, via scattered or diffuse reflections from the various optical elements.

The imaging system 600 may further comprise a processor 610. In some variations, the processor may be within the same housing as the light source assembly 602, as shown in FIG. 6A. The processor 610 may be configured to generate real-time videos. More specifically, the processor 610 may comprise, for example, a microprocessor or other suitable central processing unit. As video frames are acquired, at least a portion of them may be stored in a memory unit for record-keeping purposes and/or retrieval for analysis. The imaging system 600 may further comprise a controller, which may be embodied in, for example, a microprocessor and/or timing electronics.

The imaging system 1600 may further comprise a processor 1610. In some variations, the processor may be within the same housing as the light source assembly 1602, as shown in FIG. 6C. The processor 1610 may be configured to generate real-time videos. More specifically, the processor 1610 may comprise, for example, a microprocessor or other suitable central processing unit. As video frames are acquired, at least a portion of them may be stored in a memory unit for record-keeping purposes and/or retrieval for analysis. The imaging system 1600 may further comprise a controller, which may be embodied in, for example, a microprocessor and/or timing electronics.

In some variations, for example in variations in which a single image sensor is used to acquire both reflected light video frames and fluorescence video frames, the controller may control a timing scheme for the visible light source, the excitation light source, and the image acquisition assembly. This timing scheme may enable separation of the image signal associated with the reflected light and the image signal associated with the fluorescence emission light. In particular, the timing scheme may involve illuminating the object with illumination light and excitation light according to a pulsing scheme, and processing the reflected light image signal and fluorescence image signal with a processing scheme, wherein the processing scheme is synchronized and matched to the pulsing scheme (e.g., via a controller) to enable separation of the two image signals in a time-division multiplexed manner. Examples of such pulsing and image processing schemes have been described in U.S. Pat. No. 9,173,554, filed on Mar. 18, 2009, and titled "IMAGING SYSTEM FOR COMBINED FULL-COLOR REFLECTANCE AND NEAR-INFRARED IMAGING," the contents of which are hereby incorporated by reference in their entirety. However, other suitable pulsing and image processing schemes may be used to acquire reflected light video frames and fluorescence video frames simultaneously. Furthermore, the controller may be configured to control the timing scheme for the visible light source, the excitation light source, and the image acquisition assembly based at least in part on the relative movement between the image acquisition assembly and the object.

The image acquisition assembly 612 may acquire images using a system of optics (e.g., one or more lenses, one or more filters, one or more mirrors, beam splitters, etc.) to collect and focus light (e.g., reflected light and/or fluorescent light) onto an image sensor assembly. In some variations, the image acquisition assembly may be at least partially located in a camera head connected to the laparoscope 604. The camera head may be connected to a processor 610 via a camera port 614. The image sensor assembly may comprise at least one solid state image sensor. The one or more image sensors may include, for example, a charge coupled device (CCD), a CMOS sensor, a CID, or other suitable sensor technology. In one variation, the image sensor assembly may include a single chip, single image sensor (e.g., a grayscale image sensor or a color image sensor having an RGB color filter array deposited on its pixels).

The image acquisition assembly 1612 may acquire images using a system of optics (e.g., one or more lenses, one or more filters, one or more mirrors, beam splitters, etc.) to collect and focus light (e.g., reflected light and/or fluorescent light) onto an image sensor assembly. In some variations, the image acquisition assembly may be at least partially located in the open field camera head 1604. The open field camera head may be connected to a processor 1610 via a camera port 1614. The image sensor assembly may comprise at least one solid state image sensor. The one or more image sensors may include, for example, a charge coupled device (CCD), a CMOS sensor, a CID, or other suitable sensor technology. In one variation, the image sensor assembly may include a single chip, single image sensor (e.g., a grayscale image sensor or a color image sensor having an RGB color filter array deposited on its pixels).

Figure 8:
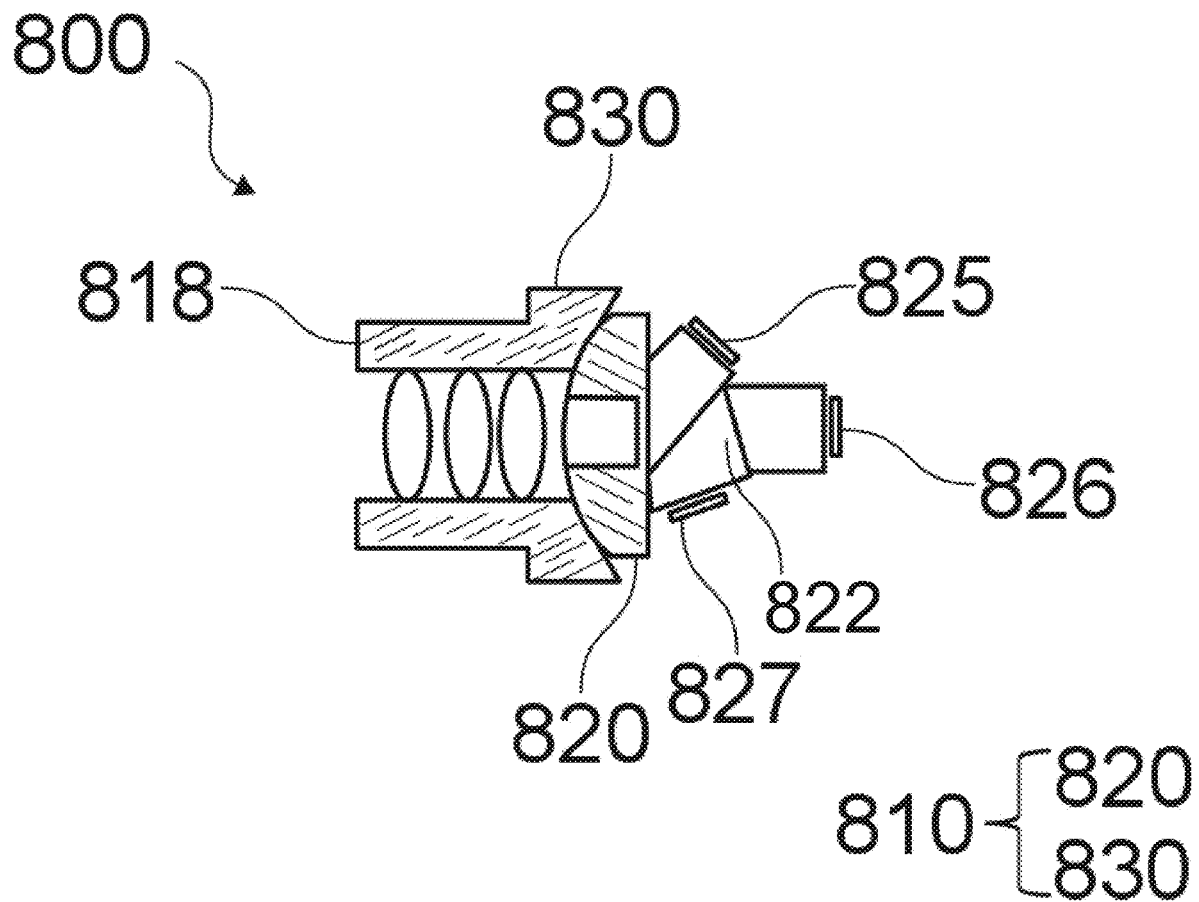
FIG. 8 shows a section view of a multi-chip image acquisition assembly comprising a multi-chip prism with an adjustable prism mount located between the camera optics and the prism according to an embodiment.

In some variations, the image sensor assembly may comprise multiple image sensors arranged, for example, on faces of a prism such as a Philips prism. FIG. 8 shows an exemplary multi-chip image acquisition assembly 800 which may comprise a camera opto-mechanical assembly 818, and an adjustable sensor mount 810 for a multi-chip image sensor assembly that includes a sensor prism 822, and multiple image sensors 825, 826, and 827. Each of the multiple sensors 825, 826, 827 may be bonded and sealed directly to their respective prism face, and the prism 822 may function in place of a closed cavity to facilitate preventing dust and debris from locating near to the image sensor surfaces. The prism 822 may be mounted to a sensor assembly platform 820 that interfaces adjustably with a fixed platform 830. The adjustable sensor mount 810 may facilitate alignment of the prism 822, and may be used with an alignment jig, bridge plates, adjustment fasteners, bonding for permanent fixation, or any other features and techniques described herein for facilitating alignment of adjustable sensor mounts.

The image sensor may be located within an adjustable sensor mount as described herein. For example, FIG. 6B shows an exemplary camera assembly 616, which may form part of an endoscopic imaging system 600 or an open field imaging system 1600, comprising an adjustable sensor mount. As shown there, the camera assembly 616 of image acquisition assembly 612 (or 1612) may comprise an adjustable sensor mount 620 and opto-mechanical assembly 618, comprising an optical system for imaging onto a sensor plane. The adjustable sensor mount 620 may comprise a closed cavity sensor assembly 622 and a platform 630. The closed cavity sensor assembly 622 and platform 630 may have the features described herein with respect to FIGS. 1-3F. In other variations, the adjustable sensor mount may have the features described herein with respect to FIGS. 5A-5D. In other variations, the adjustable sensor mount may have the features described herein with respect to FIG. 8. The platform 630 of the adjustable sensor mount 620 may be fastened to the opto-mechanical assembly 618, and the alignment of the closed cavity sensor assembly 622 relative to platform 630 may be fixed using bridge plate 650 and bridge screws 651.

After initial assembly of the camera assembly 616, the adjustable sensor mount 620 may be adjusted for tilt and/or x-y alignment. For example, the adjustment fasteners (e.g., screws) and/or adjustment tension fasteners (e.g., screws) may be tightened and/or loosened, as described herein, to adjust the tilt of the closed cavity sensor assembly 622 until the sensor is satisfactorily aligned with the imaging plane. After alignment, the alignment of the adjustable sensor mount 620 may be fixed. For example, bridge plates 650 may be attached with bridge plate screws 651 to fix the alignment. After the alignment is fixed, the fasteners may be removed. Glue or another suitable bonding agent may optionally be used for permanent fixation (e.g., glue or another suitable bonding agent may be placed around and/or adjacent the interface between the closed cavity platform and platform, and/or introduced through a port 352 in the center of one or more bridge plates).

Figure 7A:
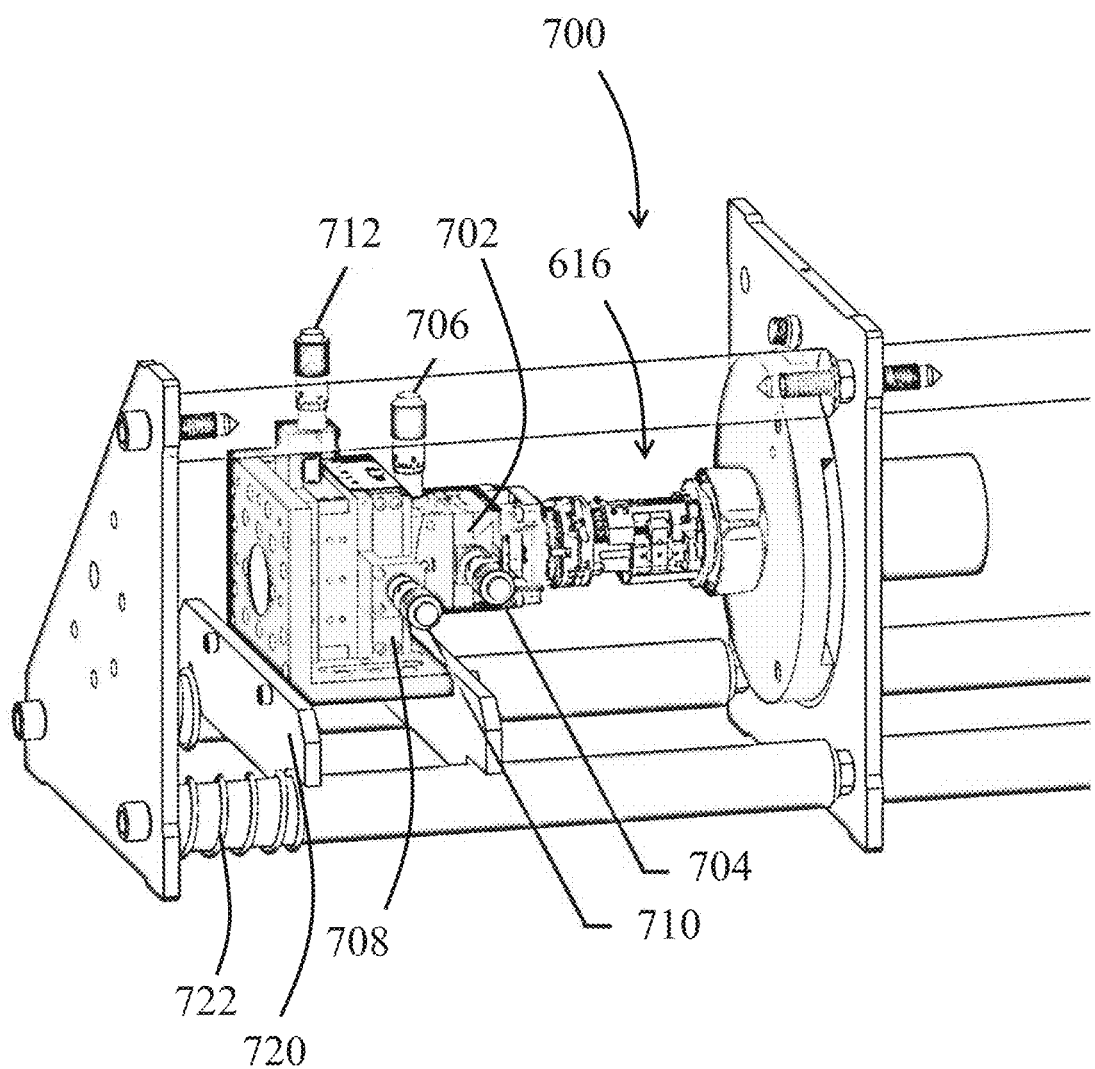
FIGS. 7A-7B show an alignment adjustment jig that may be used to align an adjustable sensor mount that is part of an imaging system according to an embodiment.
Figure 7B:
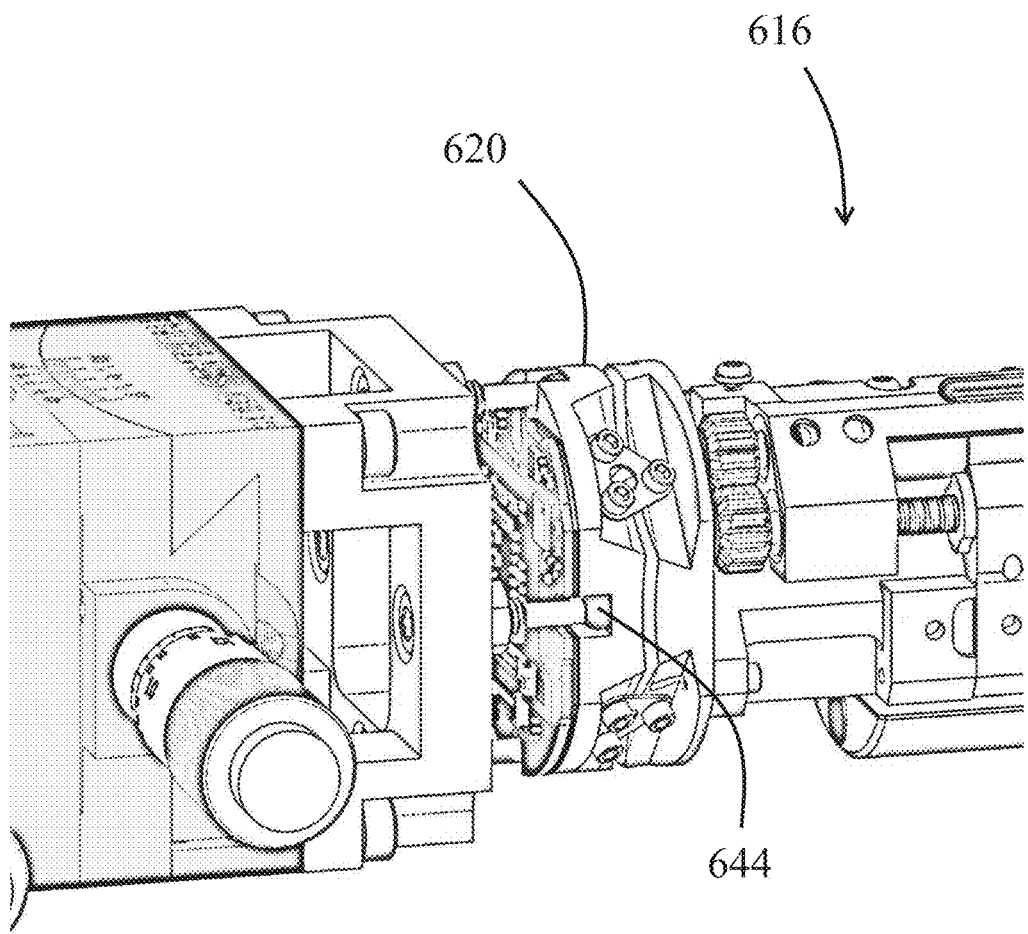

In other variations, an alignment adjustment jig may be used to align an adjustable sensor mount. FIGS. 7A-7B show an alignment adjustment jig that may be used to align an adjustable sensor mount that is part of an imaging system, such as but not limited to an endoscopic imaging system or an open field imaging system. Shown there is an alignment adjustment jig 700 configured to adjust the adjustable sensor mount 620 of camera assembly 616 shown in FIG. 6B.

FIGS. 7A-7B show the imaging device camera assembly 616 on alignment adjustment jig 700. The alignment adjustment jig 700 may be configured to separately adjust tilt and x-y alignment. A first set of stages 702 may be configured to adjust tilt using an Rx knob 704 and an Ry knob 706. These stages may be stacked with different radii, such that they have the same pivot point. A second set of stages 708 may be configured to adjust x-y alignment using an x-translation knob 710 and a y-translation knob 712.

Together, the stages 702 and 708 may form an adjustment stage assembly 720. The adjustment stage assembly 720 may be mounted on a set of rails, and may be held in place against the adjustable sensor mount 620 by compression springs 722. The adjustment stage assembly 720 may contact the rear of the closed cavity sensor assembly 622 via pin-mounted kinematic balls 644 (see FIG. 7B). The kinematic balls 644 may be located in indentations (e.g., conical indentations) in the closed cavity platform of the sensor assembly 622. After the stages have been used to move the sensor assembly 622 to align the sensor, the alignment of the sensor mount 620 may be fixed using a bridge assembly (e.g., fastening bridge plates 650 and bridge plate screws 651 to the sensor assembly 622 and platform 630).

Figure 9A:
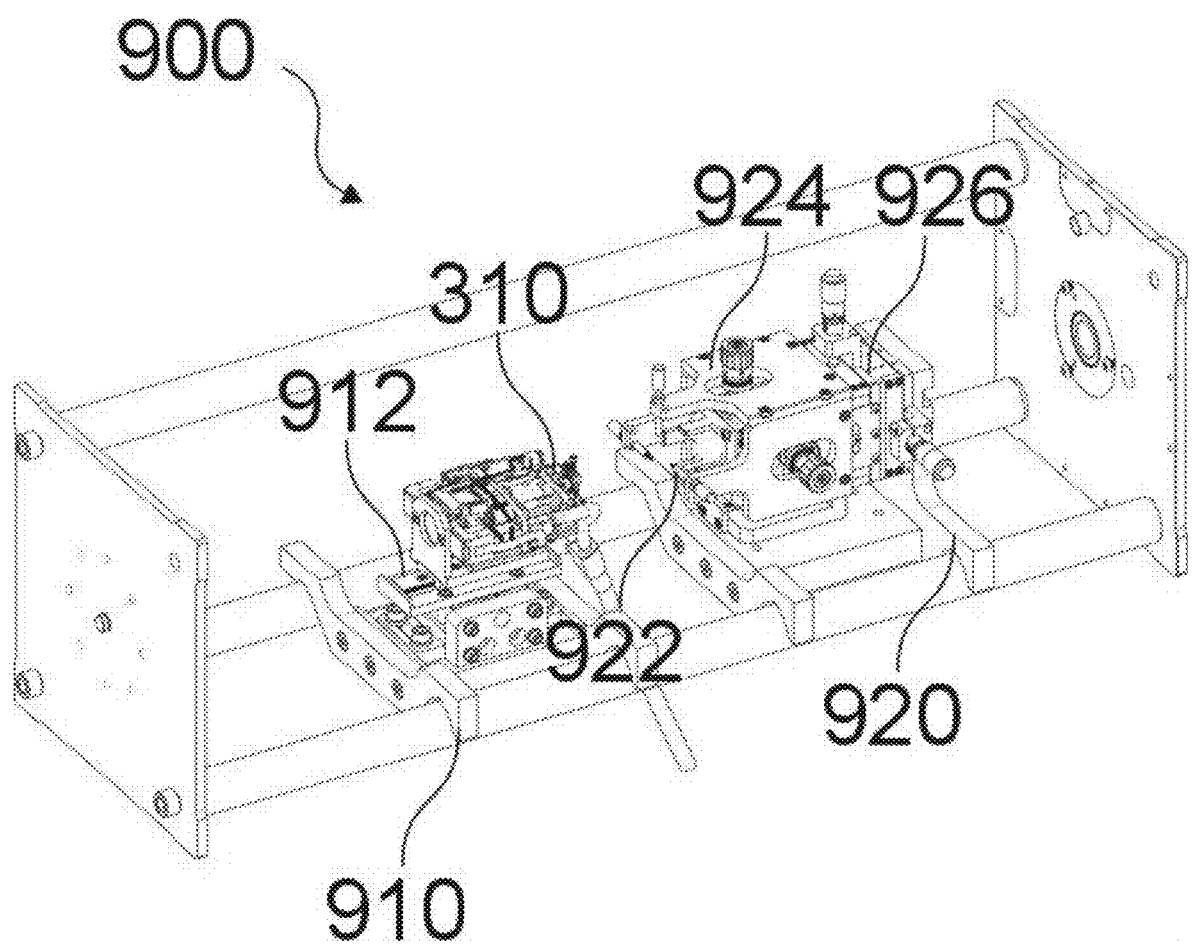
FIGS. 9A-9B show an alignment adjustment jig that may be used to align an adjustable sensor mount that is part of an imaging system according to an embodiment.
Figure 9B:
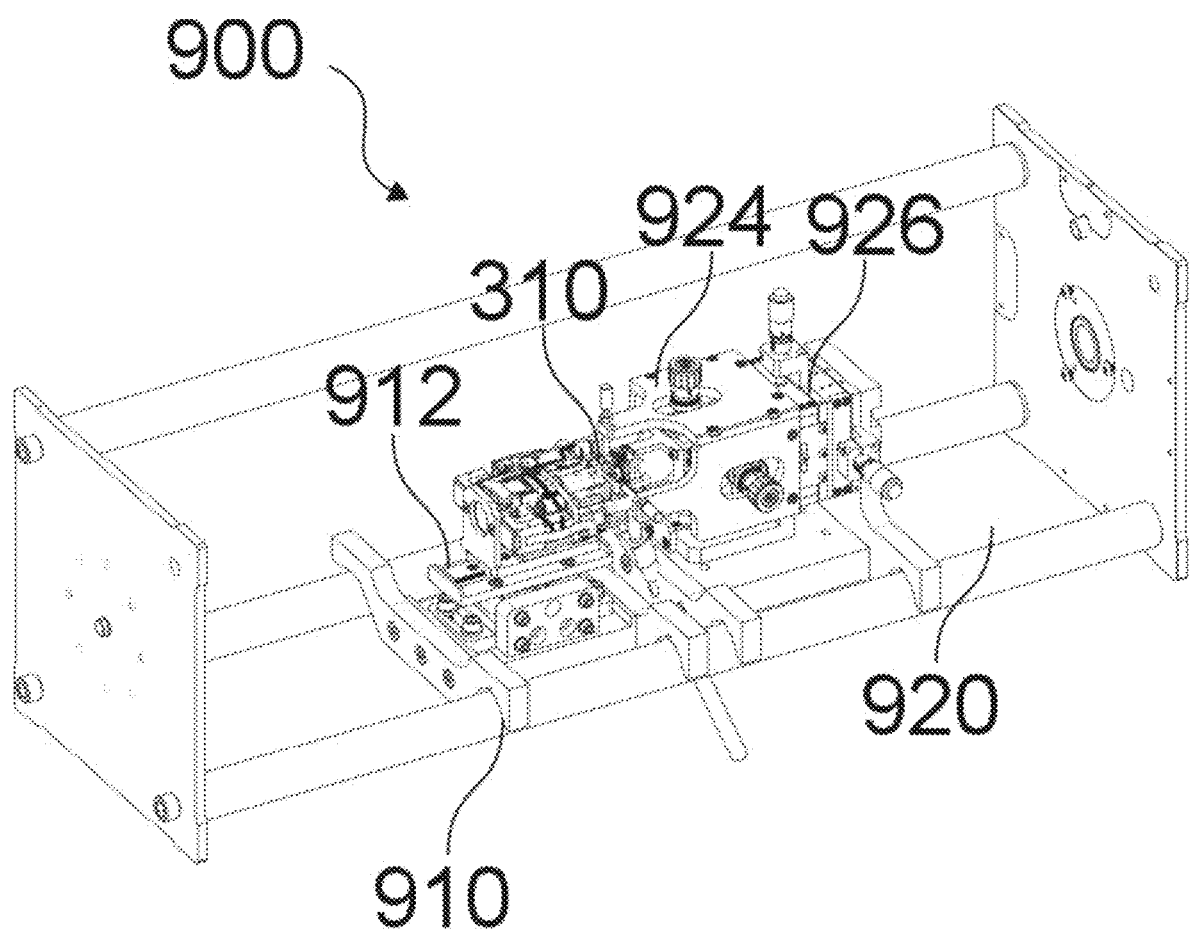

FIGS. 9A-B show an alternative alignment adjustment jig 900 that may be used to align an adjustable sensor mount. A camera assembly of an imaging system is shown comprising an adjustable sensor mount 310, and mounted to camera holder module 910 of the alignment adjustment jig 900 via focus guides slide 912. Sensor tilt adjustment module 920 is shown comprising contact pins 922 for contacting the adjustable sensor mount 310, rotational adjustment stage 924, and translational adjustment stage 926. FIG. 9B shows the rail-mounted camera holder module 910 and tilt adjustment module 920 slid together so that contact pins 922 are contacting the closed cavity platform of the adjustable sensor mount 310, so that the alignment of the closed cavity platform may be adjusted by turning the rotation and translation adjustment knobs of the tilt adjustment module 920. Focus of the camera assembly may be adjusted during the sensor alignment process by sliding the camera slightly away from or toward the adjustable sensor mount 310, prior to tightly securing the fasteners affixing the adjustable sensor mount to the camera frame.

Figure 10A:
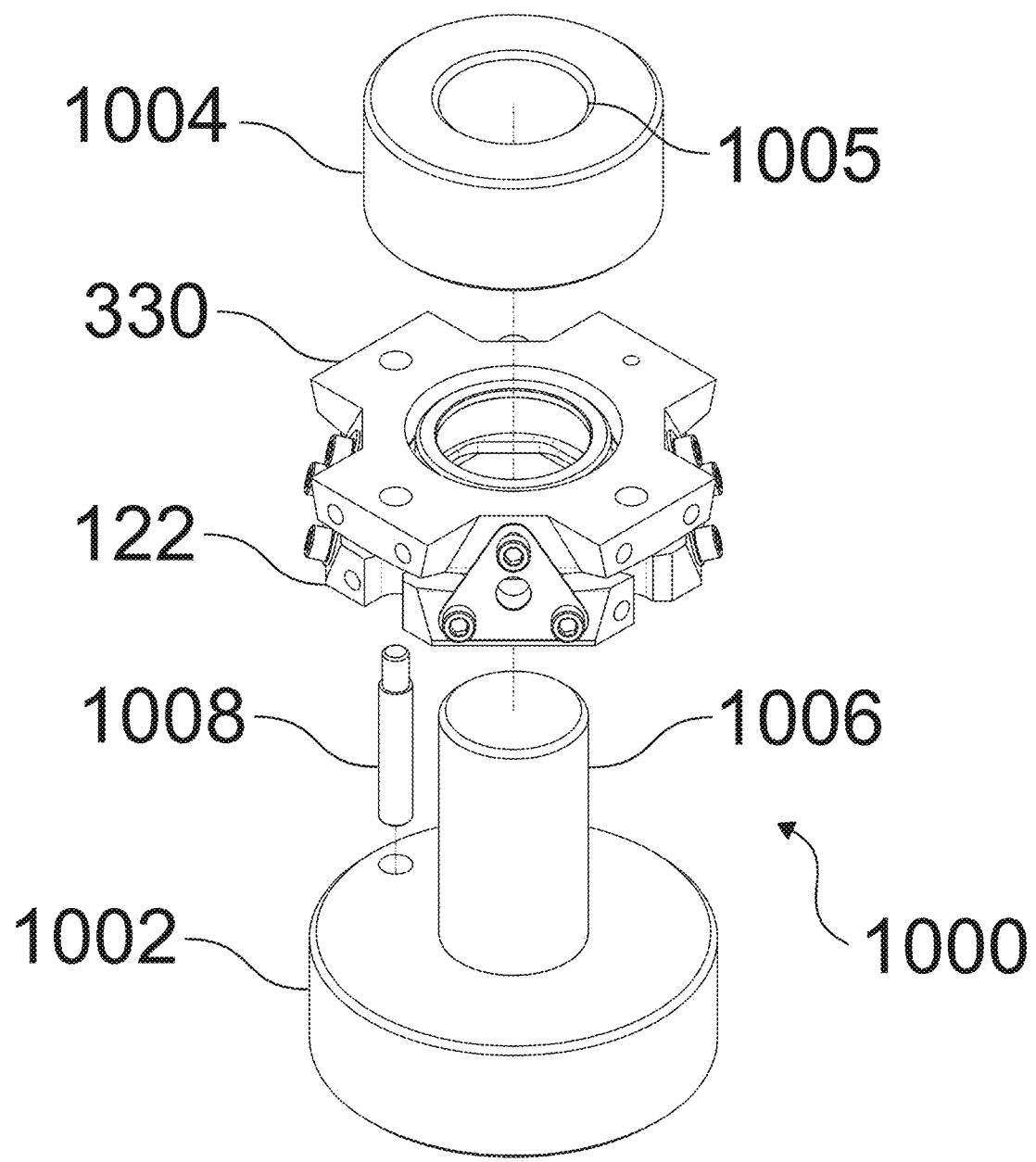
FIG. 10A shows an exploded view of an alignment adjustment jig that may be used to align an adjustable sensor mount that is part of an imaging system.
Figure 10B:
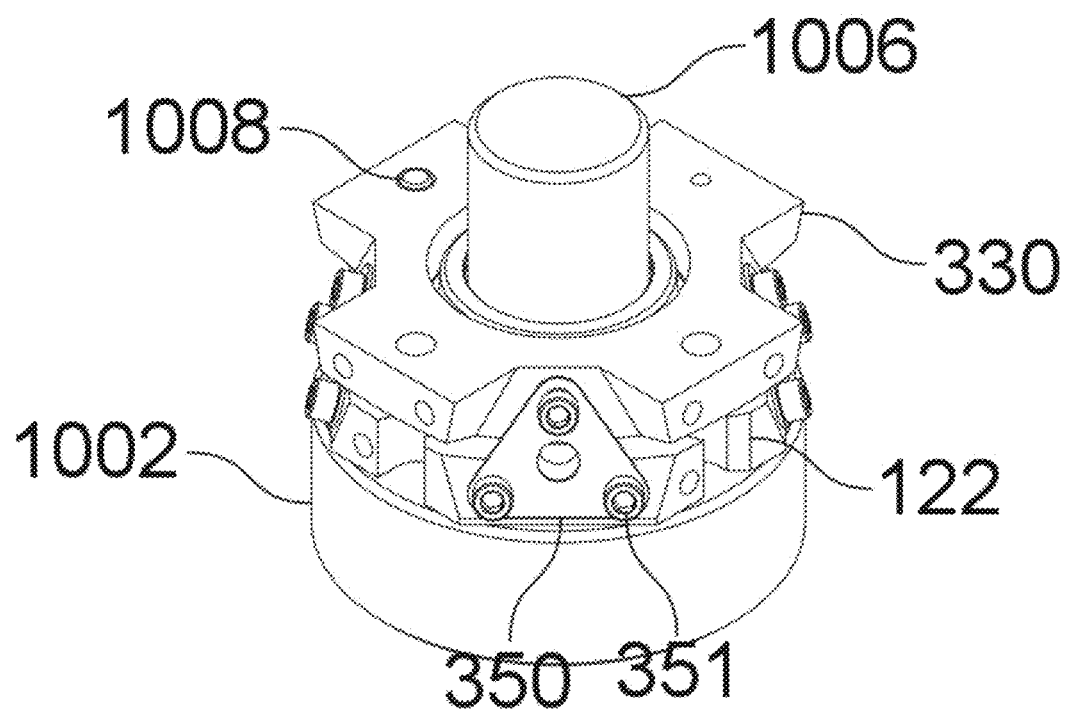
FIG. 10B shows an adjustable sensor mount in place on the alignment adjustment jig.

FIGS. 10A-B show a cylindrical alignment adjustment jig 1000 that may be used to align an adjustable sensor mount prior to sealing the closed cavity sensor assembly. The alignment adjustment jig 1000 comprises a base plate 1002 including a center pin 1006, a top plate 1004 including hole 1005 that fits precisely around center pin 1006, and an alignment pin 1008. Before placing the window 121 and sensor/PCB into the closed cavity sensor assembly 120, an adjustable sensor mount including the closed cavity platform 122 and platform 330 may be slid over center pin 1006 of base plate 1002, so that the rear flat surface of closed cavity platform 122 sits flat on the top flat surface of base plate 1002, and alignment pin 1008 may facilitate rotational alignment of the adjustable sensor mount platforms about the center axis of the jig, as shown in FIG. 10B. Hole 1005 of top plate 1004 may then be slid over center pin 1006 so that the bottom flat surface of the top plate 1004 sits flat on the top flat surface of platform 330, thus facilitating parallel alignment of the top flat surface of platform 330 and the bottom flat surface of closed cavity platform 122. Following alignment, the platforms may be reversibly fixed using a bridge assembly (e.g., fastening bridge plates 350 and bridge plate screws 351 to the closed cavity platform 122 and platform 330), so that the platform alignment is maintained while completing assembly. In some cases, further alignment adjustment may not be needed following alignment with the alignment adjustment jig 1000 and subsequent completed assembly of the adjustable sensor mount. However, in case testing of the assembled adjustable sensor mount indicates further alignment is required, fine alignment adjustment may be performed by loosening the bridge assembly fasteners slightly and performing adjustment using any tool or jig that may allow for fine adjustment, such as the alignment adjustment jigs described in reference to FIGS. 7A-B or FIGS. 9A-B herein.

The imaging systems described herein according to various embodiments may be part of a kit. A kit may include any part or parts of the systems described herein. In other variations, a kit may include any part or parts of the systems described herein and a fluorescence agent such as, for example, a fluorescence dye such as ICG or any suitable fluorescence agent or a combination of fluorescence agents. In some variations, a suitable fluorescence agent is an agent which can circulate with the blood (e.g., an agent which can circulate with, for example, a component of the blood such as plasma in the blood) and which fluoresces when exposed to appropriate excitation light energy. An example of the fluorescence agent is a fluorescence dye, which includes any non-toxic fluorescence dye. In certain variations, the fluorescence dye may include a dye that emits light in the near-infrared spectrum. In certain embodiments, the fluorescence dye may include a tricarbocyanine dye such as, for example, indocyanine green (ICG). In other variations the fluorescence dye may comprise ICG, fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, or a combination thereof, which is excitable using excitation light wavelengths appropriate to each imaging agent. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the fluorescence is derived from autofluorescence, one or more of the fluorophores giving rise to the autofluorescence may be an endogenous tissue fluorophore (e.g., collagen, elastin, NADH, etc.), 5-aminolevulinic acid (5-ALA), or a combination thereof. ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement. According to some embodiments, the fluorescence imaging agent may be administered in various concentrations to achieve a desired circulating concentration in the blood. For example, in embodiments where the fluorescence imaging agent is ICG, it may be administered at a concentration of about 2.5 mg/mL to achieve a circulating concentration of about 5 µM to about 10 µM in blood. In various embodiments, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 µM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various embodiments. In another aspect, the method excludes any step of administering the imaging agent to the subject.

In various embodiments, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the medical imaging modality.

In some variations, the fluorescence imaging agent used in combination with the methods, systems and kits described herein may be used for blood flow imaging, tissue perfusion imaging, lymphatic imaging, or a combination thereof, which may performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva).

In variations relating to cardiac applications or any vascular applications, the imaging agent(s) (e.g., ICG alone or in combination with another imaging agent) may be injected intravenously. For example, the imaging agent may be injected intravenously through the central venous line, bypass pump and/or cardioplegia line and/or other vasculature to flow and/or perfuse the coronary vasculature, microvasculature and/or grafts. ICG may be administered as a dilute ICG/blood/saline solution down the grafted vessel or other vasculature such that the final concentration of ICG in the coronary artery or other vasculature depending on application is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten ml of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis. In other variations, the methods, dosages or a combination thereof as described herein in connection with cardiac imaging may be used in any vascular and/or tissue perfusion imaging applications.

Lymphatic mapping is an important part of effective surgical staging for cancers that spread through the lymphatic system (e.g., breast, gastric, gynecological cancers). Excision of multiple nodes from a particular node basin can lead to serious complications, including acute or chronic lymphedema, paresthesia, and/or seroma formation, when in fact, if the sentinel node is negative for metastasis, the surrounding nodes will most likely also be negative. Identification of the tumor draining lymph nodes (LN) has become an important step for staging cancers that spread through the lymphatic system in breast cancer surgery for example. LN mapping involves the use of dyes and/or radiotracers to identify the LNs either for biopsy or resection and subsequent pathological assessment for metastasis. The goal of lymphadenectomy at the time of surgical staging is to identify and remove the LNs that are at high risk for local spread of the cancer. Sentinel lymph node (SLN) mapping has emerged as an effective surgical strategy in the treatment of breast cancer. It is generally based on the concept that metastasis (spread of cancer to the axillary LNs), if present, should be located in the SLN, which is defined in the art as the first LN or group of nodes to which cancer cells are most likely to spread from a primary tumor. If the SLN is negative for metastasis, then the surrounding secondary and tertiary LN should also be negative. The primary benefit of SLN mapping is to reduce the number of subjects who receive traditional partial or complete lymphadenectomy and thus reduce the number of subjects who suffer from the associated morbidities such as lymphedema and lymphocysts.

The current standard of care for SLN mapping involves injection of a tracer that identifies the lymphatic drainage pathway from the primary tumor. The tracers used may be radioisotopes (e.g. Technetium-99 or Tc-99m) for intraoperative localization with a gamma probe. The radioactive tracer technique (known as scintigraphy) is limited to hospitals with access to radioisotopes require involvement of a nuclear physician and does not provide real-time visual guidance. A colored dye, isosulfan blue, has also been used, however this dye cannot be seen through skin and fatty tissue. In addition, blue staining results in tattooing of the breast lasting several months, skin necrosis can occur with subdermal injections, and allergic reactions with rare anaphylaxis have also been reported. Severe anaphylactic reactions have occurred after injection of isosulfan blue (approximately 2% of patients). Manifestations include respiratory distress, shock, angioedema, urticarial and pruritus. Reactions are more likely to occur in subjects with a history of bronchial asthma, or subjects with allergies or drug reactions to triphenylmethane dyes. Isosulfan blue is known to interfere with measurements of oxygen saturation by pulse oximetry and methemoglobin by gas analyzer. The use of isosulfan blue may result in transient or long-term (tattooing) blue coloration.

In contrast, fluorescence imaging in accordance with the various embodiments for use in SLN visualization, mapping, facilitates direct real-time visual identification of a LN and/or the afferent lymphatic channel intraoperatively, facilitates high-resolution optical guidance in real-time through skin and fatty tissue, visualization of blood flow, tissue perfusion or a combination thereof.

In some variations, visualization, classification or both of lymph nodes during fluorescence imaging may be based on imaging of one or more imaging agents, which may be further based on visualization and/or classification with a gamma probe (e.g., Technetium Tc-99m is a clear, colorless aqueous solution and is typically injected into the periareolar area as per standard care), another conventionally used colored imaging agent (isosulfan blue), and/or other assessment such as, for example, histology. The breast of a subject may be injected, for example, twice with about 1% isosulfan blue (for comparison purposes) and twice with an ICG solution having a concentration of about 2.5 mg/ml. The injection of isosulfan blue may precede the injection of ICG or vice versa. For example, using a TB syringe and a 30 G needle, the subject under anesthesia may be injected with 0.4 ml (0.2 ml at each site) of isosulfan blue in the periareolar area of the breast. For the right breast, the subject may be injected at 12 and 9 o'clock positions and for the left breast at 12 and 3 o'clock positions. The total dose of intradermal injection of isosulfan blue into each breast may be about 4.0 mg (0.4 ml of 1% solution: 10 mg/ml). In another exemplary variation, the subject may receive an ICG injection first followed by isosulfan blue (for comparison). One 25 mg vial of ICG may be reconstituted with 10 ml sterile water for injection to yield a 2.5 mg/ml solution immediately prior to ICG administration. Using a TB syringe and a 30 G needle, for example, the subject may be injected with about 0.1 ml of ICG (0.05 ml at each site) in the periareolar area of the breast (for the right breast, the injection may be performed at 12 and 9 o'clock positions and for the left breast at 12 and 3 o'clock positions). The total dose of intradermal injection of ICG into each breast may be about 0.25 mg (0.1 ml of 2.5 mg/ml solution) per breast. ICG may be injected, for example, at a rate of 5 to 10 seconds per injection. When ICG is injected intradermally, the protein binding properties of ICG cause it to be rapidly taken up by the lymph and moved through the conducting vessels to the LN. In some variations, the ICG may be provided in the form of a sterile lyophilized powder containing 25 mg ICG with no more than 5% sodium iodide. The ICG may be packaged with aqueous solvent consisting of sterile water for injection, which is used to reconstitute the ICG. In some variations the ICG dose (mg) in breast cancer sentinel lymphatic mapping may range from about 0.5 mg to about 10 mg depending on the route of administration. In some variations, the ICG does may be about 0.6 mg to about 0.75 mg, about 0.75 mg to about 5 mg, about 5 mg to about 10 mg. The route of administration may be for example subdermal, intradermal (e.g., into the periareolar region), subareolar, skin overlaying the tumor, intradermal in the areola closest to tumor, subdermal into areola, intradermal above the tumor, periareolar over the whole breast, or a combination thereof. The NIR fluorescent positive LNs (e.g., using ICG) may be represented as a black and white NIR fluorescence image(s) for example and/or as a full or partial color (white light) image, full or partial desaturated white light image, an enhanced colored image, an overlay (e.g., fluorescence with any other image), a composite image (e.g., fluorescence incorporated into another image) which may have various colors, various levels of desaturation or various ranges of a color to highlight/visualize certain features of interest. Processing of the images may be further performed for further visualization and/or other analysis (e.g., quantification). The lymph nodes and lymphatic vessels may be visualized (e.g., intraoperatively, in real time) using fluorescence imaging systems and methods according to the various embodiments for ICG and SLNs alone or in combination with a gamma probe (Tc-99m) according to American Society of Breast Surgeons (ASBrS) practice guidelines for SLN biopsy in breast cancer patients. Fluorescence imaging for LNs may begin from the site of injection by tracing the lymphatic channels leading to the LNs in the axilla. Once the visual images of LNs are identified, LN mapping and identification of LNs may be done through incised skin, LN mapping may be performed until ICG visualized nodes are identified. For comparison, mapping with isosulfan blue may be performed until 'blue' nodes are identified. LNs identified with ICG alone or in combination with another imaging technique (e.g., isosulfan blue, and/or Tc-99m) may be labeled to be excised. Subject may have various stages of breast cancer (e.g., IA, IB, IIA).

In some variations, such as for example, in gynecological cancers (e.g., uterine, endometrial, vulvar and cervical malignancies), ICG may be administered interstitially for the visualization of lymph nodes, lymphatic channels, or a combination thereof. When injected interstitially, the protein binding properties of ICG cause it to be rapidly taken up by the lymph and moved through the conducting vessels to the SLN. ICG may be provided for injection in the form of a sterile lyophilized powder containing 25 mg ICG (e.g., 25 mg/vial) with no more than 5.0% sodium iodide. ICG may be then reconstituted with commercially available water (sterile) for injection prior to use. According to an embodiment, a vial containing 25 mg ICG may be reconstituted in 20 ml of water for injection, resulting in a 1.25 mg/ml solution. A total of 4 ml of this 1.25 mg/ml solution is to be injected into a subject (4×1 ml injections) for a total dose of ICG of 5 mg per subject. The cervix may also be injected four (4) times with a 1 ml solution of 1% isosulfan blue 10 mg/ml (for comparison purposes) for a total dose of 40 mg. The injection may be performed while the subject is under anesthesia in the operating room. In some variations the ICG dose (mg) in gynecological cancer sentinel lymph node detection and/or mapping may range from about 0.1 mg to about 5 mg depending on the route of administration. In some variations, the ICG does may be about 0.1 mg to about 0.75 mg, about 0.75 mg to about 1.5 mg, about 1.5 mg to about 2.5 mg, about 2.5 mg to about 5 mg. The route of administration may be for example cervical injection, vulva peritumoral injection, hysteroscopic endometrial injection, or a combination thereof. In order to minimize the spillage of isosulfan blue or ICG interfering with the mapping procedure when LNs are to be excised, mapping may be performed on a hemi-pelvis, and mapping with both isosulfan blue and ICG may be performed prior to the excision of any LNs. LN mapping for Clinical Stage I endometrial cancer may be performed according to the NCCN Guidelines for Uterine Neoplasms, SLN Algorithm for Surgical Staging of Endometrial Cancer; and SLN mapping for Clinical Stage I cervical cancer may be performed according to the NCCN Guidelines for Cervical Neoplasms, Surgical/SLN Mapping Algorithm for Early-Stage Cervical Cancer. Identification of LNs may thus be based on ICG fluorescence imaging alone or in combination or co-administration with for a colorimetric dye (isosulfan blue) and/or radiotracer.

Visualization of lymph nodes may be qualitative and/or quantitative. Such visualization may comprise, for example, lymph node detection, detection rate, anatomic distribution of lymph nodes. Visualization of lymph nodes according to the various embodiments may be used alone or in combination with other variables (e.g., vital signs, height, weight, demographics, surgical predictive factors, relevant medical history and underlying conditions, histological visualization and/or assessment, Tc-99m visualization and/or assessment, concomitant medications). Follow-up visits may occur on the date of discharge, and subsequent dates (e.g., one month).

Lymph fluid comprises high levels of protein, thus ICG can bind to endogenous proteins when entering the lymphatic system. Fluorescence imaging (e.g., ICG imaging) for lymphatic mapping when used in accordance with the methods and systems described herein offers the following example advantages: high-signal to background ratio (or tumor to background ratio) as NIR does not generate significant autofluorescence, real-time visualization feature for lymphatic mapping, tissue definition (i.e., structural visualization), rapid excretion and elimination after entering the vascular system, and avoidance of non-ionizing radiation. Furthermore, NIR imaging has superior tissue penetration (approximately 5 to 10 millimeters of tissue) to that of visible light (1 to 3 mm of tissue). The use of ICG for example also facilitates visualization through the peritoneum overlying the para-aortic nodes. Although tissue fluorescence can be observed with NIR light for extended periods, it cannot be seen with visible light and consequently does not impact pathologic evaluation or processing of the LN. Also, florescence is easier to detect intraoperatively than blue staining (isosulfan blue) of lymph nodes. In other variations, the methods, dosages or a combination thereof as described herein in connection with lymphatic imaging may be used in any vascular and/or tissue perfusion imaging applications.

Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. In some embodiments, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement.

One or more embodiments are directed to a fluorescence imaging agent for use in the imaging systems and methods as described herein. In one or more embodiments, the use may comprise blood flow imaging, tissue perfusion imaging, lymphatic imaging, or a combination thereof, which may occur during an invasive surgical procedure, a minimally invasive surgical procedure, a non-invasive surgical procedure, or a combination thereof. The fluorescence agent may be included in the kit described herein.

In one or more embodiments, the invasive surgical procedure may comprise a cardiac-related surgical procedure or a reconstructive surgical procedure. The cardiac-related surgical procedure may comprise a cardiac coronary artery bypass graft (CABG) procedure which may be on pump and/or off pump.

In one or more embodiments, the minimally invasive or the non-invasive surgical procedure may comprise a wound care procedure.

In one or more embodiments, the lymphatic imaging may comprise identification of a lymph node, lymph node drainage, lymphatic mapping, or a combination thereof. The lymphatic imaging may relate to the female reproductive system.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated.

Accordingly, it will be understood by those of skill in the art that various changes in form and details may be made without departing from the spirit and scope of the present invention as set forth in the following.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description features are described herein as part of the same or separate embodiments, however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

The invention claimed is:

1. An adjustable sensor mount system for aligning a sensor with a lens assembly of an imaging system, comprising:
   a flexure assembly comprising a top sensor mount plane, wherein the top sensor mount plane is configured to tilt about at least one axis with respect to the lens assembly of the imaging system, wherein the tilting of the top sensor mount plane is caused via a force applied to a side of the flexure assembly, and
   an adjustable sensor mount mounted to the flexure assembly, wherein the adjustable sensor mount comprises a closed cavity sensor assembly that comprises the sensor, such that tilting of the top sensor mount plane causes the sensor to tilt about the at least one axis with respect to the lens assembly of the imaging system.

2. The adjustable sensor mount system of claim 1, wherein the flexure assembly comprises one or more flexure blades configured to deform to cause the tilting of the flexure assembly about at least one axis.

3. The adjustable sensor mount system of claim 1, wherein the adjustable sensor mount comprises a flexure plate connecting the closed cavity sensor assembly to an X-Y platform of the adjustable sensor mount, such that a deformation of the flexure plate allows tilting of the closed cavity sensor assembly with respect to the X-Y platform.

4. The adjustable sensor mount system of claim 3, wherein a movement of the X-Y platform allows translation of the closed cavity sensor assembly in at least one translational direction with respect to the flexure assembly.

5. The adjustable sensor mount system of claim 4, wherein the at least one translational direction comprises two translational directions along which the sensor is configured to be translated via the movement of the X-Y platform.

6. The adjustable sensor mount system of claim 3, wherein the flexure plate comprises a plurality of channels through the flexure plate, wherein the plurality of channels separate an inner region of the flexure plate from an outer region of the flexure plate.

7. The adjustable sensor mount system of claim 3, wherein the deformation of the flexure plate allows tilting of the closed cavity sensor assembly with respect to the X-Y platform in two perpendicular directions.

8. The adjustable sensor mount system of claim 1, wherein the at least one axis comprises two axes about which the sensor is configured to be tilted via a movement of the flexure assembly.

9. The adjustable sensor mount system of claim 1, wherein the adjustable sensor mount is mounted to the top sensor mount plane of the flexure assembly.

10. The adjustable sensor mount system of claim 1, further comprising one or more fasteners, wherein the one or more fasteners are configured to apply the force to the side of the flexure assembly.

11. The adjustable sensor mount system of claim 10, wherein the one or more fasteners comprise one or more screws.

12. The adjustable sensor mount system of claim 1, wherein at least a portion of the closed cavity sensor assembly comprises a ultraviolet (UV)-transmitting material to allow for transmission of a ultraviolet (UV) light to illuminate a ultraviolet (UV)-activated bonding glue.

13. The adjustable sensor mount system of claim 12, wherein the UV-transmitting material comprises glass.

* * * * *